United States Patent
Bergman et al.

(10) Patent No.: US 12,254,628 B2
(45) Date of Patent: *Mar. 18, 2025

(54) SYSTEMS AND METHODS FOR REVIEW OF COMPUTER-AIDED DETECTION OF PATHOLOGY IN IMAGES

(71) Applicant: BENEVIS INFORMATICS, LLC, Marietta, GA (US)

(72) Inventors: Harris Bergman, Marietta, GA (US); Mark Blomquist, Tucson, AZ (US); Michael Wimmer, Prescott, AZ (US)

(73) Assignee: BENEVIS INFORMATICS, LLC, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/641,941

(22) Filed: Apr. 22, 2024

(65) Prior Publication Data

US 2024/0303814 A1 Sep. 12, 2024

Related U.S. Application Data

(63) Continuation of application No. 18/510,197, filed on Nov. 15, 2023, which is a continuation of application
(Continued)

(51) Int. Cl.
*G06T 7/00* (2017.01)
*A61B 6/00* (2006.01)
(Continued)

(52) U.S. Cl.
CPC .............. *G06T 7/0012* (2013.01); *A61B 6/51* (2024.01); *A61B 6/5217* (2013.01);
(Continued)

(58) Field of Classification Search
CPC ......... G06T 7/0012; G06T 2207/10116; G06T 2207/20081; G06T 2207/20084;
(Continued)

(56) References Cited

U.S. PATENT DOCUMENTS

| 5,594,638 A | 1/1997 | Illiff |
| 5,660,176 A | 8/1997 | Illiff |

(Continued)

OTHER PUBLICATIONS

PCT/US2019/032096, International Search Report and Written Opinion issued on Jul. 29, 2019, 8 pages.
(Continued)

*Primary Examiner* — Van D Huynh
(74) *Attorney, Agent, or Firm* — Meunier Carlin & Curfman LLC

(57) ABSTRACT

Disclosed and described herein are systems and methods of performing computer-aided detection (CAD)/diagnosis (CADx) in medical images and comparing the results of the comparison. Such detection can be used for treatment plans and verification of claims produced by healthcare providers, for the purpose of identifying discrepancies between the two. In particular, embodiments disclosed herein are applied to identifying dental caries ("caries") in radiographs and comparing them against progress notes, treatment plans, and insurance claims.

30 Claims, 22 Drawing Sheets

Related U.S. Application Data

No. 17/055,411, filed as application No. PCT/US2019/032096 on May 15, 2019, now Pat. No. 11,823,376.

(60) Provisional application No. 62/672,266, filed on May 16, 2018.

(51) Int. Cl.
  *A61B 6/51* (2024.01)
  *A61B 8/00* (2006.01)
  *A61B 5/055* (2006.01)
  *A61B 6/03* (2006.01)

(52) U.S. Cl.
  CPC ............ *A61B 8/5223* (2013.01); *A61B 5/055* (2013.01); *A61B 6/032* (2013.01); *A61B 6/037* (2013.01); *G06T 2207/10116* (2013.01); *G06T 2207/20081* (2013.01); *G06T 2207/20084* (2013.01); *G06T 2207/30036* (2013.01)

(58) Field of Classification Search
  CPC ............ G06T 2207/30036; A61B 6/51; A61B 6/5217; A61B 8/5223; A61B 5/055; A61B 6/032; A61B 6/037
  See application file for complete search history.

(56) References Cited

U.S. PATENT DOCUMENTS

| | | |
|---|---|---|
| 5,711,297 A | 1/1998 | Iliff |
| 5,724,968 A | 3/1998 | Iliff |
| 5,742,700 A | 4/1998 | Yoon et al. |
| 5,868,669 A | 2/1999 | Iliff |
| 5,915,036 A | 6/1999 | Grunkin |
| 6,058,322 A | 5/2000 | Nishikawa et al. |
| 6,113,540 A | 9/2000 | Illiff |
| 6,125,194 A | 9/2000 | Yeh et al. |
| 6,195,474 B1 | 2/2001 | Snyder et al. |
| 6,201,880 B1 | 3/2001 | Elbaum et al. |
| 6,206,829 B1 | 3/2001 | Illiff |
| 6,283,761 B1 | 9/2001 | Joao |
| 6,292,596 B1 | 9/2001 | Snyder et al. |
| 6,482,156 B2 | 11/2002 | Iliff |
| 6,654,728 B1 | 11/2003 | Li et al. |
| 6,760,468 B1 | 7/2004 | Yeh et al. |
| 6,879,712 B2 | 4/2005 | Tuncay et al. |
| 6,925,198 B2 | 8/2005 | Scharlack et al. |
| 7,010,153 B2 | 3/2006 | Zimmermann |
| 7,215,803 B2 | 5/2007 | Marshall |
| 7,245,753 B2 | 7/2007 | Squilla et al. |
| 7,283,654 B2 | 10/2007 | McLain |
| 7,292,716 B2 | 11/2007 | Kim |
| 7,297,111 B2 | 11/2007 | Iliff |
| 7,300,402 B2 | 11/2007 | Iliff |
| 7,306,560 B2 | 12/2007 | Illiff |
| 7,308,126 B2 | 12/2007 | Rogers et al. |
| 7,324,680 B2 | 1/2008 | Zimmermann |
| 7,362,890 B2 | 4/2008 | Scharlack et al. |
| 7,433,505 B2 | 10/2008 | Yoo et al. |
| 7,457,443 B2 | 11/2008 | Persky |
| 7,463,757 B2 | 12/2008 | Luo et al. |
| 7,464,040 B2 | 12/2008 | Joao |
| 7,471,821 B2 | 12/2008 | Rubbert et al. |
| 7,490,048 B2 | 2/2009 | Joao |
| 7,499,588 B2 | 3/2009 | Jacobs et al. |
| 7,532,942 B2 | 5/2009 | Reiner et al. |
| 7,551,760 B2 | 6/2009 | Scharlack et al. |
| 7,577,284 B2 | 8/2009 | Wong et al. |
| 7,603,000 B2 | 10/2009 | Zheng et al. |
| 7,620,228 B2 | 11/2009 | Yoo et al. |
| 7,623,693 B2 | 11/2009 | Holzner et al. |
| 7,648,460 B2 | 1/2010 | Simopoulos et al. |
| 7,702,139 B2 | 4/2010 | Liang et al. |
| 7,751,606 B2 | 7/2010 | Luo et al. |
| 7,756,326 B2 | 7/2010 | Howerton, Jr. |
| 7,783,094 B2 | 8/2010 | Collins et al. |
| 7,835,558 B2 | 11/2010 | Gagnon et al. |
| 7,840,042 B2 | 11/2010 | Kriveshko et al. |
| 7,844,091 B2 | 11/2010 | Wong et al. |
| 7,844,092 B2 | 11/2010 | Crucs |
| 7,853,476 B2 | 12/2010 | Reiner et al. |
| 7,860,289 B2 | 12/2010 | Yoo et al. |
| 7,865,261 B2 | 1/2011 | Pfeiffer |
| 7,912,257 B2 | 3/2011 | Paley et al. |
| 7,916,900 B2 | 3/2011 | Lanier |
| 7,936,911 B2 | 5/2011 | Fang et al. |
| 7,940,260 B2 | 5/2011 | Kriveshko |
| 7,957,573 B2 | 6/2011 | Ikeda |
| 8,014,576 B2 | 9/2011 | Collins et al. |
| 8,015,138 B2 | 9/2011 | Iliff |
| 8,035,637 B2 | 10/2011 | Kriveshko |
| 8,036,438 B2 | 10/2011 | Komiya |
| 8,045,772 B2 | 10/2011 | Kosuge et al. |
| 8,077,949 B2 | 12/2011 | Liang et al. |
| 8,087,932 B2 | 1/2012 | Liu et al. |
| 8,099,268 B2 | 1/2012 | Kitching et al. |
| 8,117,549 B2 | 2/2012 | Reiner |
| 8,144,954 B2 | 3/2012 | Quadling et al. |
| 8,145,340 B2 | 3/2012 | Taub et al. |
| RE43,433 E | 5/2012 | Iliff |
| 8,199,988 B2 | 6/2012 | Marshall et al. |
| 8,208,704 B2 | 6/2012 | Wong et al. |
| RE43,548 E | 7/2012 | Iliff |
| 8,224,045 B2 | 7/2012 | Burns et al. |
| 8,270,689 B2 | 9/2012 | Liang et al. |
| 8,275,180 B2 | 9/2012 | Kuo |
| 8,303,301 B2 | 11/2012 | Bergersen |
| 8,320,634 B2 | 11/2012 | Deutsch |
| 8,335,694 B2 | 12/2012 | Reiner |
| 8,341,100 B2 | 12/2012 | Miller et al. |
| 8,385,617 B2 | 2/2013 | Okawa et al. |
| 8,391,574 B2 | 3/2013 | Collins et al. |
| 8,411,917 B2 | 4/2013 | Gandyra |
| 8,416,984 B2 | 4/2013 | Liang et al. |
| 8,417,010 B1 | 4/2013 | Colby |
| 8,433,033 B2 | 4/2013 | Harata et al. |
| 8,442,283 B2 | 5/2013 | Choi |
| 8,442,927 B2 | 5/2013 | Chakradhar et al. |
| 8,447,078 B2 | 5/2013 | Maschke |
| 8,447,087 B2 | 5/2013 | Wong et al. |
| 8,494,241 B2 | 7/2013 | Kadobayashi et al. |
| 8,520,925 B2 | 8/2013 | Duret |
| 8,532,355 B2 | 9/2013 | Quadling et al. |
| 8,556,625 B2 | 10/2013 | Lovely |
| 8,571,281 B2 | 10/2013 | Wong et al. |
| 8,577,493 B2 | 11/2013 | Taub et al. |
| 8,605,973 B2 | 12/2013 | Wang et al. |
| 8,605,974 B2 | 12/2013 | Liang et al. |
| 8,634,631 B2 | 1/2014 | Kanerva et al. |
| 8,737,706 B2 | 5/2014 | Graham et al. |
| 8,768,025 B2 | 7/2014 | Wong et al. |
| 8,768,036 B2 | 7/2014 | Caligor et al. |
| 8,848,991 B2 | 9/2014 | Tjioe et al. |
| 8,867,800 B2 | 10/2014 | Bullis et al. |
| 8,897,526 B2 | 11/2014 | MacLeod et al. |
| 8,913,814 B2 | 12/2014 | Gandyra |
| 8,914,097 B2 | 12/2014 | Burlina et al. |
| 8,977,020 B2 | 3/2015 | Goto |
| 8,977,023 B2 | 3/2015 | Buckland |
| 8,977,025 B2 | 3/2015 | Baumgart |
| 8,977,049 B2 | 3/2015 | Aila et al. |
| 8,979,773 B2 | 3/2015 | Hirabayashi |
| 8,983,029 B2 | 3/2015 | Hasegawa |
| 8,983,162 B2 | 3/2015 | Ye et al. |
| 8,983,165 B2 | 3/2015 | Sun et al. |
| 8,989,347 B2 | 3/2015 | Sperl et al. |
| 8,989,461 B2 | 3/2015 | Zhu et al. |
| 8,989,473 B2 | 3/2015 | Nambu |
| 8,989,474 B2 | 3/2015 | Kido et al. |
| 8,989,487 B2 | 3/2015 | Choe et al. |
| 8,989,514 B2 | 3/2015 | Russakoff et al. |
| 8,994,747 B2 | 3/2015 | Heron |
| 8,996,428 B2 | 3/2015 | Baras et al. |

(56) References Cited

U.S. PATENT DOCUMENTS

| | | |
|---|---|---|
| 9,001,967 B2 | 4/2015 | Baturin et al. |
| 9,001,972 B2 | 4/2015 | Takahashi et al. |
| 9,002,084 B2 | 4/2015 | Shahar et al. |
| 9,005,119 B2 | 4/2015 | Iliff |
| 9,014,423 B2 | 4/2015 | Wang et al. |
| 9,014,440 B2 | 4/2015 | Arumugam et al. |
| 9,014,442 B2 | 4/2015 | Kelly et al. |
| 9,014,447 B2 | 4/2015 | Slabaugh et al. |
| 9,014,454 B2 | 4/2015 | Zankowski |
| 9,014,455 B2 | 4/2015 | Oh et al. |
| 9,019,301 B2 | 4/2015 | Matsue et al. |
| 9,020,220 B2 | 4/2015 | Nukui |
| 9,020,221 B2 | 4/2015 | Liu et al. |
| 9,020,222 B2 | 4/2015 | Wiets |
| 9,020,223 B2 | 4/2015 | Liu et al. |
| 9,020,228 B2 | 4/2015 | Yan et al. |
| 9,020,232 B2 | 4/2015 | Graham |
| 9,020,235 B2 | 4/2015 | Krishnan et al. |
| 9,020,236 B2 | 4/2015 | Wang et al. |
| 9,025,726 B2 | 5/2015 | Ishii |
| 9,025,842 B2 | 5/2015 | Barr et al. |
| 9,025,849 B2 | 5/2015 | Fouras et al. |
| 9,026,193 B2 | 5/2015 | Pahlevan et al. |
| 9,030,492 B2 | 5/2015 | Bischoff et al. |
| 9,031,295 B2 | 5/2015 | Klingenbeck |
| 9,031,300 B1 | 5/2015 | Manjeshwar et al. |
| 9,031,302 B2 | 5/2015 | Omi |
| 9,031,303 B2 | 5/2015 | Yamaguchi |
| 9,036,882 B2 | 5/2015 | Masumoto et al. |
| 9,036,884 B2 | 5/2015 | Harvey et al. |
| 9,036,887 B2 | 5/2015 | Fouras et al. |
| 9,036,899 B2 | 5/2015 | Vandenberghe |
| 9,041,712 B2 | 5/2015 | Bogues et al. |
| 9,042,611 B2 | 5/2015 | Blezek et al. |
| 9,042,612 B2 | 5/2015 | Gkanatsios et al. |
| 9,042,613 B2 | 5/2015 | Spilker et al. |
| 9,042,627 B2 | 5/2015 | Ohishi et al. |
| 9,042,628 B2 | 5/2015 | Florent et al. |
| 9,111,223 B2 | 8/2015 | Schmidt et al. |
| 9,111,372 B2 | 8/2015 | Ortega et al. |
| 9,262,698 B1 | 2/2016 | George et al. |
| 9,277,877 B2 | 3/2016 | Burlina et al. |
| 9,333,060 B2 | 5/2016 | Hunter |
| 9,346,167 B2 | 5/2016 | O'Connor et al. |
| 9,373,059 B1 | 6/2016 | Heifets et al. |
| 9,430,697 B1 | 8/2016 | Iliadis et al. |
| 9,443,141 B2 | 9/2016 | Mirowski et al. |
| 9,443,192 B1 | 9/2016 | Cosic |
| 9,445,713 B2 | 9/2016 | Douglas et al. |
| 9,532,762 B2 | 1/2017 | Cho et al. |
| 9,536,054 B1 | 1/2017 | Podilchuk et al. |
| 9,542,621 B2 | 1/2017 | He et al. |
| 9,547,804 B2 | 1/2017 | Nirenberg et al. |
| 9,569,736 B1 | 2/2017 | Ghesu et al. |
| 9,589,374 B1 | 3/2017 | Gao et al. |
| 9,595,002 B2 | 3/2017 | Leeman-Munk et al. |
| 9,633,282 B2 | 4/2017 | Sharma et al. |
| 9,659,560 B2 | 5/2017 | Cao et al. |
| 9,662,040 B2 | 5/2017 | Kam et al. |
| 9,665,927 B2 | 5/2017 | Ji et al. |
| 9,668,699 B2 | 6/2017 | Georgescu et al. |
| 9,672,814 B2 | 6/2017 | Cao et al. |
| 9,674,447 B2 | 6/2017 | Kam et al. |
| 9,684,960 B2 | 6/2017 | Buzaglo et al. |
| 9,697,463 B2 | 7/2017 | Ross et al. |
| 9,700,219 B2 | 7/2017 | Sharma et al. |
| 9,710,748 B2 | 7/2017 | Ross et al. |
| 9,715,508 B1 | 7/2017 | Kish et al. |
| 9,717,417 B2 | 8/2017 | DiMaio |
| 9,720,515 B2 | 8/2017 | Wagner et al. |
| 9,730,643 B2 | 8/2017 | Georgescu et al. |
| 9,734,567 B2 | 8/2017 | Zhang et al. |
| 9,747,546 B2 | 8/2017 | Ross et al. |
| 9,747,548 B2 | 8/2017 | Ross et al. |
| 9,749,738 B1 | 8/2017 | Adsumilli et al. |
| 9,750,450 B2 | 9/2017 | Shie et al. |
| 9,753,959 B2 | 9/2017 | Birdwell et al. |
| 9,760,807 B2 | 9/2017 | Zhou et al. |
| 9,767,385 B2 | 9/2017 | Nguyen et al. |
| 9,767,557 B1 | 9/2017 | Gulsun et al. |
| 9,779,492 B1 | 10/2017 | Garnavi et al. |
| 9,792,531 B2 | 10/2017 | Georgescu et al. |
| 9,792,907 B2 | 10/2017 | Bocklet et al. |
| 9,798,751 B2 | 10/2017 | Birdwell et al. |
| 9,805,255 B2 | 10/2017 | Yang et al. |
| 9,805,303 B2 | 10/2017 | Ross |
| 9,805,304 B2 | 10/2017 | Ross |
| 9,805,466 B2 | 10/2017 | Ryu et al. |
| 9,811,906 B1 | 11/2017 | Vizitiu et al. |
| 9,818,029 B2 | 11/2017 | Lee et al. |
| 11,553,874 B2 | 1/2023 | Hillen |
| 2006/0069591 A1 | 3/2006 | Razzano |
| 2006/0233455 A1* | 10/2006 | Cheng ............... G01R 33/56563 |
| | | 382/274 |
| 2008/0170764 A1* | 7/2008 | Burns .................. A61B 5/0088 |
| | | 382/128 |
| 2011/0110575 A1 | 5/2011 | Banumathi et al. |
| 2012/0087468 A1* | 4/2012 | Lang ...................... A61B 6/505 |
| | | 378/56 |
| 2012/0189182 A1* | 7/2012 | Liang .................... A61C 19/00 |
| | | 382/128 |
| 2014/0037180 A1* | 2/2014 | Wang .................... G06T 7/0012 |
| | | 382/132 |
| 2016/0256121 A1* | 9/2016 | Colby .................... A61B 6/463 |
| 2016/0259994 A1 | 9/2016 | Ravindran et al. |
| 2016/0361037 A1* | 12/2016 | Im ........................ A61B 6/5217 |
| 2019/0269485 A1* | 9/2019 | Elbaz ................. A61B 1/00016 |
| 2019/0313963 A1* | 10/2019 | Hillen .................. G06V 10/764 |
| 2019/0333627 A1* | 10/2019 | Johnson ................. G06N 3/048 |
| 2020/0320685 A1* | 10/2020 | Anssari Moin ...... G06V 10/454 |
| 2021/0106229 A1* | 4/2021 | Van Der Poel ........... G06T 7/12 |

OTHER PUBLICATIONS

Oksana Bandura, How Dental Imaging Can Be Improved with Machine Learning, Convolutional neural networks and other machine learning algorithms are gradually transforming our reality. Dentistry is no exception. May 11, 2017. available on-line at: How_Dental_Imaging_Can_Be_Improved_with_Machine_Learning_(mddionline. com).

Office Action in connection to U.S. Appl. No. 18/510,197, dated Jul. 30, 2024.

* cited by examiner

CAD agrees with progress notes

CAD disagrees with progress notes

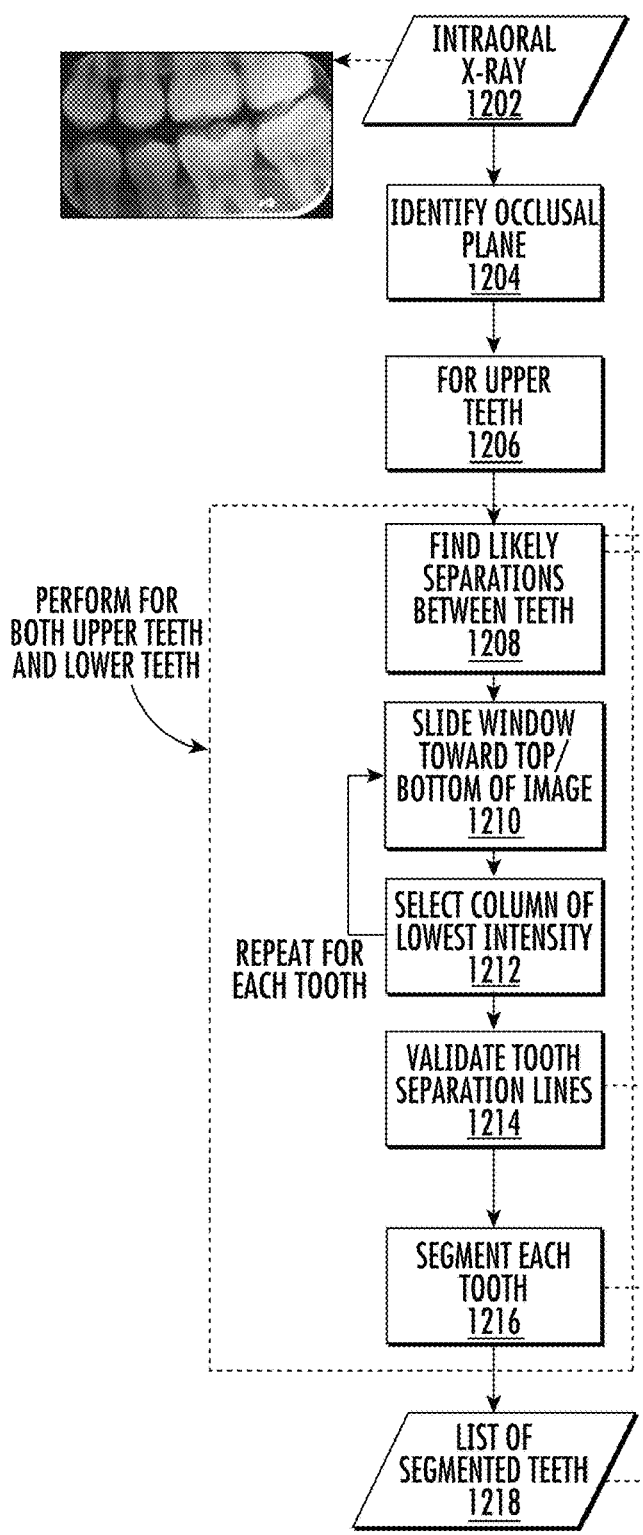
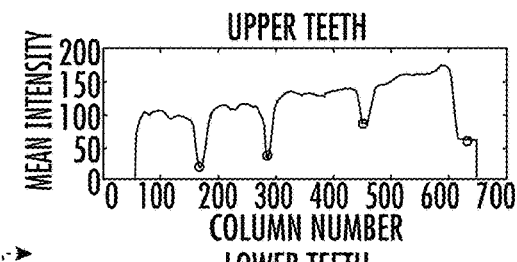
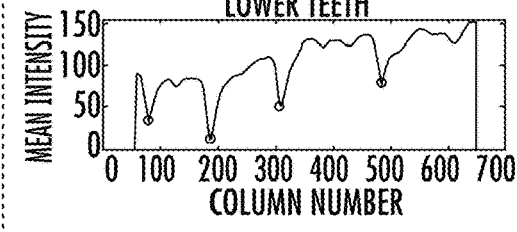
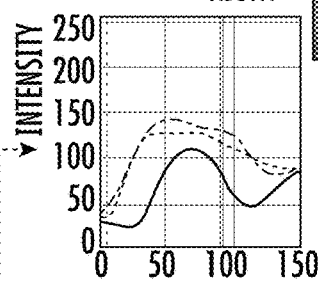
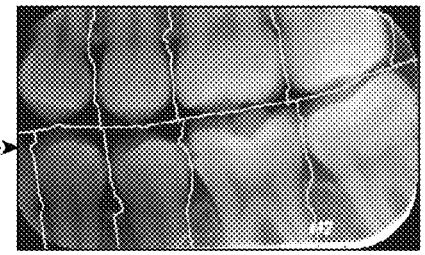
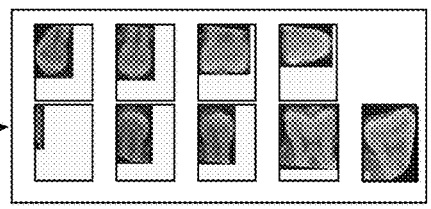
FIG. 12B
FIG. 12C
FIG. 12D
FIG. 12E
FIG. 12A
FIG. 12F Original tooth image Left-side tooth image Right-side tooth image

SYSTEMS AND METHODS FOR REVIEW OF COMPUTER-AIDED DETECTION OF PATHOLOGY IN IMAGES

CROSS-REFERENCE TO RELATED APPLICATIONS

This application is a continuation application of U.S. application Ser. No. 18/510,197 filed Nov. 15, 2023, which is a continuation application of U.S. application Ser. No. 17/055,411 filed Nov. 13, 2020, which issued as U.S. Pat. No. 11,823,376 on Nov. 21, 2023, which is a national phase under 35 U.S.C. § 371 of PCT/US2019/032096 filed on May 15, 2019, which claims priority to and benefit of U.S. provisional patent application Ser. No. 62/672,266 filed May 16, 2018, all of which are all fully incorporated by reference and made a part hereof in their entireties.

FIELD OF THE INVENTION

Embodiments of the present invention relate generally to systems and methods of comparing the results of computer-aided detection/diagnosis of pathology in medical images. Such detection can be used for treatment plans and verification of claims produced by healthcare providers, for the purpose of identifying discrepancies between the results of the computer-aided detection/diagnosis and the provider. In particular, embodiments disclosed herein are applied to identifying dental caries ("caries") in radiographs and comparing them against progress notes, treatment plans, and insurance claims.

BACKGROUND

Interpretation of medical images is not a perfect science. For example, radiologists typically fail to identify lung cancer nodules in more than half of chest X-rays. Studies have also shown that radiologists miss 30-50% of breast cancers in mammograms. Because of the shortcomings associated with humans reading medical images, there has been substantial interest in computer-aided detection (CAD) and computer-aided diagnosis (CADx) of medical images.

Cancerous lesions, however, are not the only pathology that is frequently misdiagnosed. Various studies have shown that interproximal caries—decay originating from the surfaces between the teeth—are missed in dental X-rays 10-50% of the time, with 30% being the most commonly reported statistic. These studies have also shown that 30% of restorations performed following the diagnosis of interproximal caries are unfounded. The field of dentistry can benefit from having CAD/CADx tools in dental practices, yet heretofore there has been little attention given to development of CAD systems for dentistry.

Since the Logicon Caries Detector was approved by the FDA for use in 1998, there have not been any other known commercialized caries CAD systems. There are a few reasons that may explain why the demand for dental CAD products is low. A dentist may not know that his or her X-ray diagnostic ability needs improvement. A dentist that does know, may not see any financial incentive to purchase the software: recall that 30% of restorative procedures for interproximal caries, which is a significant source of revenue for a dental practice, are not validated by X-ray evidence. Accordingly, the caries detector's use has not been widespread.

Payers (e.g., insurance companies, etc.), on the other hand, have significant financial incentive to identify providers with poor diagnostic accuracy, as unnecessary dental work poses immediate expense and missed decay poses more expensive restorative work later. A leading dental auditor has shown that 4 of the 8 leading sources of fraud, waste, and abuse among dental claims, such as up-coding multi-surface restorations, are detectible in X-ray images. Unfortunately, the current mechanism for auditing claims is archaic and not scalable.

Adjudication of insurance claims for many dental procedures requires the attachment of supporting radiographs, intraoral camera pictures, or both to have the claim accepted. These images are typically submitted electronically from the provider to a third-party service for delivery to the Payer. The Payers' claims adjudicators, most of whom are neither radiologists nor dentists, are expected to examine the images to make sure that they properly document the claim. The adjudicator should have the skill and training to determine, for example, that a radiograph of the patient's left molars do not support a claim submitted for a three-surface restoration on an upper-right molar. However, the adjudicator is unlikely to have the skill to note that there was no sign of distal decay on a correct radiograph. This is one reason why up-coding of multi-surface restorations is largely undetected.

Close examination of radiographs is time-intensive and the types of claims that receive detailed review by a dentist must be prioritized. As a result, only 25% of claims for multi-surface restorations are reviewed at all and thus Payers (or the patients themselves) frequently overpay for this procedure. In certain circumstances, a Payer will refer claims to a recovery audit contractor (RAC) to perform a thorough audit of one or more claims performed by a provider. The RAC typically is paid a percentage of the claims that are identified as being unjustified. However, this is a time-consuming and expensive process.

Embodiments described herein address the shortcomings of dental imaging, detection and diagnosis, and related claims processing described above. First, embodiments of the disclosed systems and methods assist a medical professional (dentist, doctor, etc.) in detecting pathologies during the patient's examination. Second, embodiments of the disclosed systems and methods identify medical professionals who are outliers in, for example, mis-diagnosing pathologies relative to their peers. Third, embodiments of the disclosed systems and methods can be used to perform automated chart audits of claims for many procedures that are documentable with medical images.

BRIEF SUMMARY

Generally, disclosed and described herein are systems and methods that for comparing computer-aided detection (CAD) and/or diagnoses (CADx) using an image to medical records and insurance claims. In one aspect the method comprises receiving, from an image acquisition device, at least one image; and determining, by a processor, whether a pathology is present or absent in the image.

Other objects and advantages will become apparent to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 12A is a flowchart illustrating a tooth segmentation algorithm.

FIGS. 12B-12F are illustrations associated with the flowchart of FIG. 12A.

DETAILED DESCRIPTION

Figure 1A:
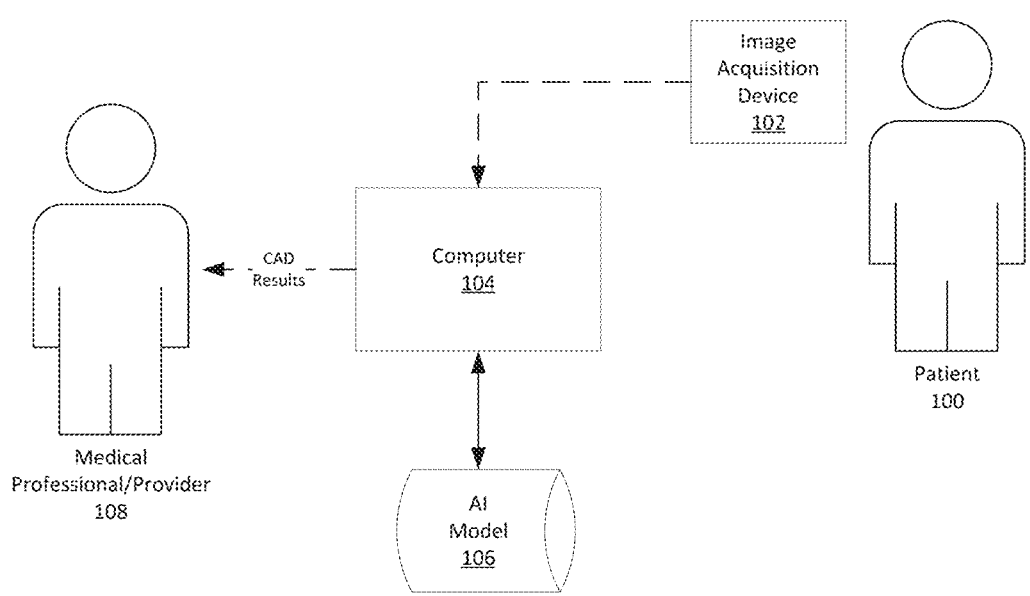
FIG. 1A. Illustrates an exemplary overview system for performing aspects of the disclosed embodiments.

Before the present methods and systems are disclosed and described, it is to be understood that the methods and systems are not limited to specific synthetic methods, specific components, or to particular compositions. It is also to be understood that the terminology used in this entire application is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, to "about" another particular value, or from "about" one value to "about" another value. When such a range is expressed, another embodiment includes from the one particular value, to the other particular value, or from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

In this document, the terms "X-ray" and "radiograph" are used interchangeably. Strictly speaking, a radiograph is the image of a person's anatomy as acquired by an X-ray imaging system. The particular modality referenced in the preferred embodiment is bite-wing radiographs acquired by computed- or digital radiography systems. Nonetheless, the embodiments for dental applications may be used on digitized film radiographs, panoramic radiographs, and cephalometric radiographs. The general medical imaging application of the embodiment can utilize radiographs and other sources of medical images, such as MRI, CT, ultrasound, PET, and SPECT machines.

When referring to the image-related information that a provider attaches to a claim, the plural form of "X-ray" or "image" will be used for brevity instead of stating "one or more X-rays" or "one or more images." In practice, a provider may attach more than one X-ray image files to support the claim.

Use of the word "claim" follows the same style as "X-ray," as it is possible for multiple claims to be submitted, for example, to a primary and secondary insurer.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, DVD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

A. Overview

FIG. 1A Illustrates an exemplary overview system for performing aspects of the disclosed embodiments. In FIG. 1A, an image of a pathology of a patient 100 is acquired by an image acquisition device 102 such as an X-ray, MRI, CT, ultrasound, PET, SPECT machine, and the like. The acquired image is then transferred to a computing device 104. In some instances, the image acquisition device 102 may be directly connected to the computer 104, while in other instances the image may be acquired by the image capture device 102 and then transferred (e.g., manually or electronically) to the computer 104.

Once received by the computer 104, computer-aided detection (CAD) and/or computer-aided diagnostics (CADx) are performed on the image. As further described herein, this may comprise segmentation of the image and using trained artificial intelligence and/or machine learning (collectively, "AI model") algorithms to make the diagnoses based on the image. The AI model 106 may be trained using a database of images, where the database has images that are associated with the pathology under consideration, as well as images that are free of the pathology under consideration. For example, the acquired image may be an X-ray of teeth, and the AI model 106 may have been trained using a database of X-rays of teeth-some with caries, and some without. The AI model 106 then determines whether the teeth in the acquired X-ray have caries, or don't have caries, based on its training.

The results of the CAD or CADx are then provided to the medical professional/provider 108, who can treat the patient 100 and/or make a claim to an insurer or other Payer based on the CAD or CADx.

Figure 1B:
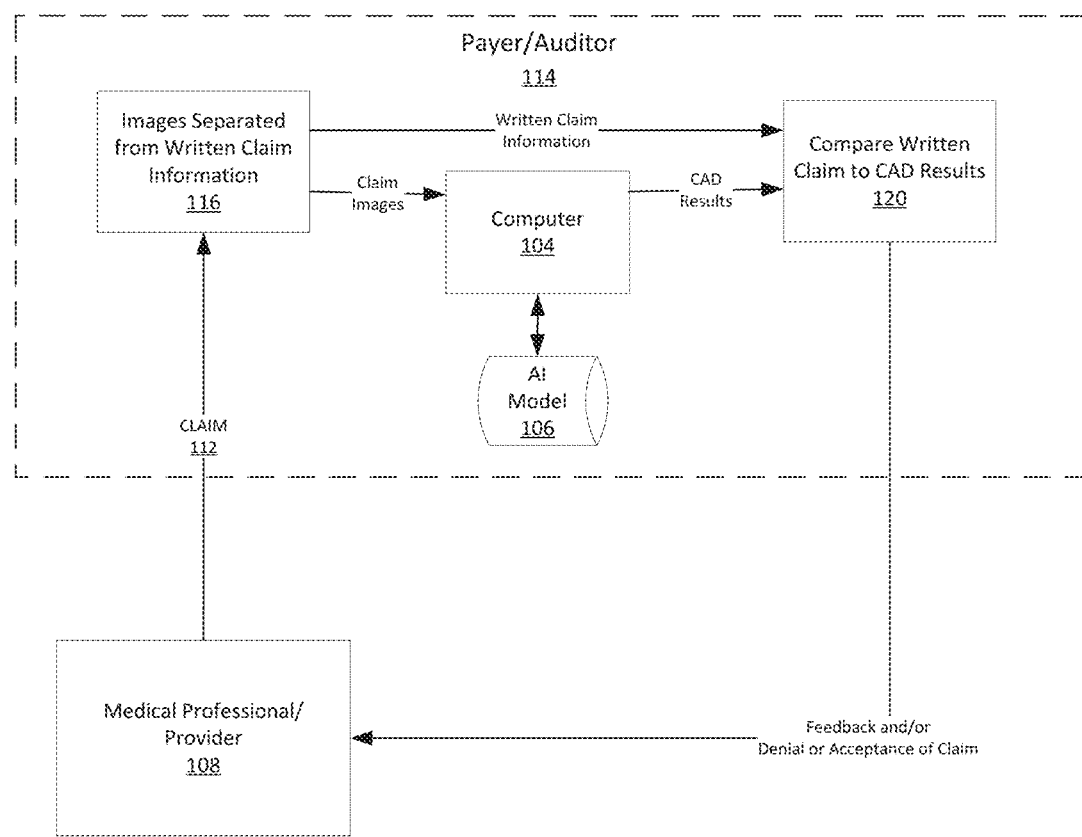
FIG. 1B illustrates another aspect of the disclosed embodiments.

FIG. 1B illustrates another aspect of the disclosed embodiments. In this aspect, a medical professional/provider 108 such as a medical or dental provider, submits a claim 112 to a Payer or an auditor 114. The claim 112 is for work performed by the medical professional/provider 108, and generally the claim 112 is comprised of two portions: (1) diagnosis/diagnostics, treatment and billing information (collectively referred to herein as "written information," which includes electronically entered, transferred and/or transmitted information) and (2) one or more images. The received claim 112 is, at 116, separated into its two components, the written information and claim images. The claim images are analyzed using the computer 104, as described above. At 120, the results of the CAD and/or CADx analysis are compared to the written claim information. The results of this comparison can then be provided to the medical professional/provider 108 as feedback, and/or can be used to pay (in part or whole) or deny (in part or whole), the claim 112.

Consider an example embodiment where the object of the system and method is to detect interproximal caries, late-stage decay, and abscesses in intraoral X-rays, and to audit the corresponding insurance claims to determine if the radiographs support the claims. Generally, this embodiment involves three steps: (1) A dentist performs an exam where radiographs are acquired, diagnoses a pathology requiring a restorative procedure, and submits a claim to an insurer; (2) software running on a computer performs CAD of caries (or other pathology) on the dental X-rays associated with that exam and procedure, and identifies what pathology is present for which tooth; and (3) software running on a computer compares the detected pathology to a diagnosis or procedure made by the provider and reports on the findings of the comparison for the exam; these findings can be aggregated to provide an assessment of the provider relative to other providers.

Step (1), above, represents the typical workflow for an appointment with a dentist. The dentist performs an oral examination on the patient and reviews X-rays. (One variation is to have the CAD results overlaid on the images of the X-rays; for example, having circles placed around detected caries on the X-ray images). If the dentist diagnoses the patient as having caries on one or more teeth and surfaces, the dentist adds a progress note to an Electronic Health Record (EHR) indicating the findings and recommended treatment. After treatment is performed, a record of the procedure is sent to the insurance provider as a claim. Supporting radiographs will also be sent to the Payer.

In step (2), the CAD step, the images are transmitted to a web service for processing. The teeth are identified using image processing algorithms that segment each tooth from the rest of the image. (Image segmentation being the term for partitioning an image into multiple regions.) For each segmented tooth, a combination of machine learning and fuzzy logic assigns a tooth number based on the Universal Numbering System. (These numbers can be converted from to the ISO 3950 or another notation system.) The order in which the numbering and classification processes occurs may be swapped. A CNN-based machine learning algorithm classifies each tooth as either having caries or not. The CAD algorithms produce a list of which teeth have caries and where on an X-ray these teeth are visible. This output is transmitted back to the sender of the images via the web service.

Steps (2) and (3) may occur prior to a provider's transmitting the images and claims to the Payer and third-party image-claim attachment service, or it may occur when the third-party image-claim attachment service receives the images, or when the Payer receives the images and claims. These two steps need not be executed on the same computer. In the first case, the CAD step is performed on the image and the CAD findings are added to the record that accompanies the image when they are sent from the provider; step (3) occurs when the Payer receives the images and relates them to their corresponding claim. In the latter case, steps (2) and (3) occur when the Payer has both the image and claim.

In another embodiment, the CAD step is performed prior to the dentist's interpreting the X-rays and examining the patient. When the CAD results are produced, the system annotates the images with markers that indicate the locations of any detected pathology. The findings may also be added to an Electronic Health Record. The dentist can then view the CAD findings as a part of his/her examination of the patient and use this additional information to assist with making a diagnosis. The CAD information can accompany the X-rays or chart when they are transmitted to a Payer or third-party image-claim attachment service. Regardless of whether the CAD step is performed prior to the provider's sending the images, the CAD step can be performed again as described in the first embodiment.

In another embodiment, the CAD step is performed on the computer on which the images are stored instead of needing to be sent to the web service. For example, the CAD software may be executed on the same computer on which the dentist views the radiographs, on a computer managed by a third-party image-claim attachment service, or on a server managed by the Payer.

In another embodiment, the system is architected for the purpose of comparing the diagnostic quality of multiple doctors in a provider network, such as a Dental Support Organization (DSO). In this embodiment the entity that reviews the dentist's diagnostic performance is not the Payer. Rather, it is an auditor or quality analyst from within the organization. The three aforementioned steps in the embodiment are therefore modified to reflect that the Payer is no longer part of the process: (1) a dentist performs an exam where X-rays are acquired, diagnoses a pathology requiring a restorative procedure, and indicates the procedure in progress notes contained in an electronic health record; (2) the X-rays and progress notes are stored in a common image archive and electronic health records system, respectively; (3) software running on a computer performs CAD of caries (or other pathology) on the dental X-rays associated with that exam and procedure, and identifies what pathology is present for which tooth; (4) software running on a computer compares the detected pathology to a diagnosis or procedure made by each dentist over a period of time and produces a report whereby an auditor or quality analyst can assess the diagnostic performance of each dentist relative to the set of dentists inside the organization.

A more generalized perspective of this provider-auditing embodiment is a system and method to use CAD to detect one or more pathologies in a medical image and compare the findings to a medical record. In these embodiments, the source of the image could be an MRI or CT scanner, digital radiography system, or other medical imaging modality. After acquisition, the images are stored on a PACS system and later viewed by a radiologist on an imaging workstation. The radiologist interprets the images and enters a report into a radiology information system (RIS). Either the radiologist or a billing specialist at the radiology practice will enter one or more ICD diagnosis codes. When a radiologist audit is performed, a batch process is run using a web service, where the medical images and ICD codes from an RIS are sent to a CAD-and-compare service, and the service responds with an indication of whether the two agree or disagree.

An embodiment of this invention for claims adjudication based on medical images differs from that of the dental embodiment because the provider who interprets the medical images is generally not the provider who performs a medical procedure (e.g., surgery) based on the diagnosis. In this embodiment, therefore, the CAD and claim comparison occurs when a claim is electronically filed for a medical procedure—as identified by its CPT (Current Procedural Terminology) code—for which a radiology report and the accompanying ICD-10 code are included in supporting documentation. The Payer transmits the CPT codes along with the supporting images (which were transmitted to the Payer) to a web service, where a CAD process interprets the image, compares the findings against the CPT code, and responds with an indication of whether the CAD results and CPT code agree.

FIGS. 1A and 1B and the above description are only non-limiting examples of applications of the embodiments of systems and methods, which are described in greater detail herein.

B. Details

Figure 2A:
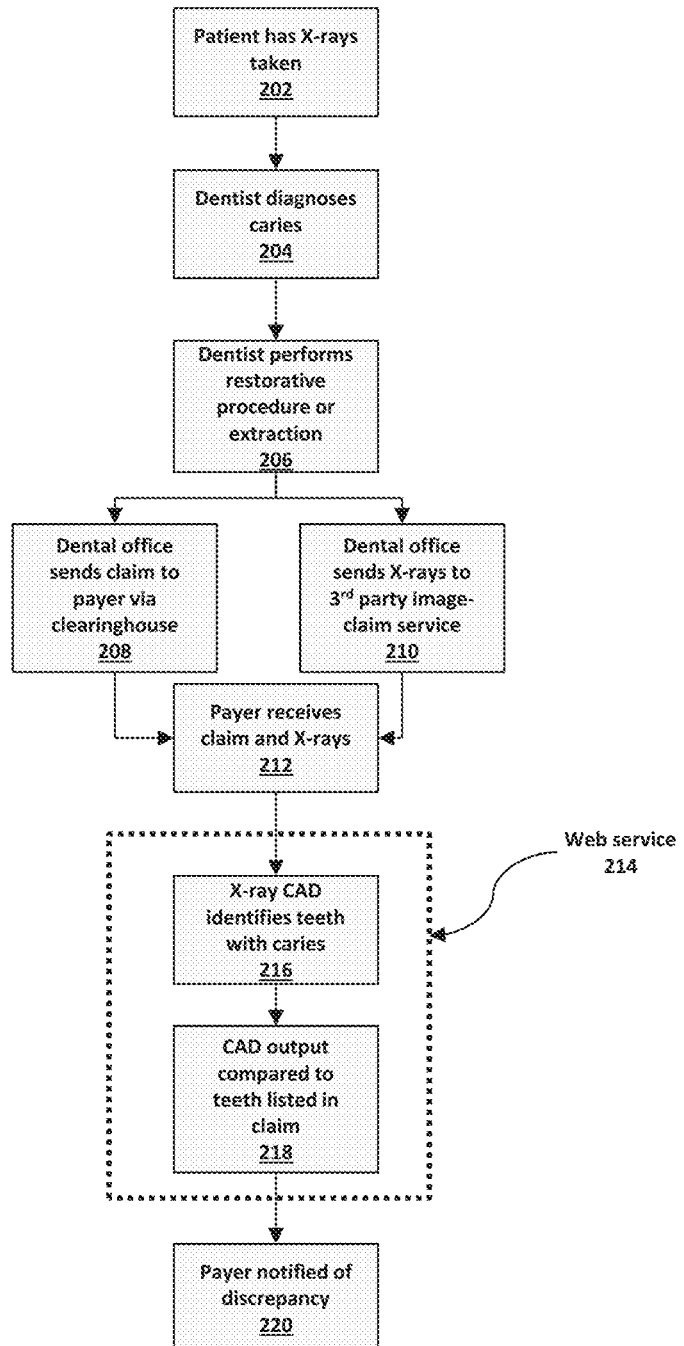
FIG. 2A is a flowchart illustrating one of the embodiments of the process, starting from when a patient has X-rays taken at an office appointment to the Payer being notified of a discrepancy between pathology on the X-ray and the reimbursement claim.
Figure 2B:
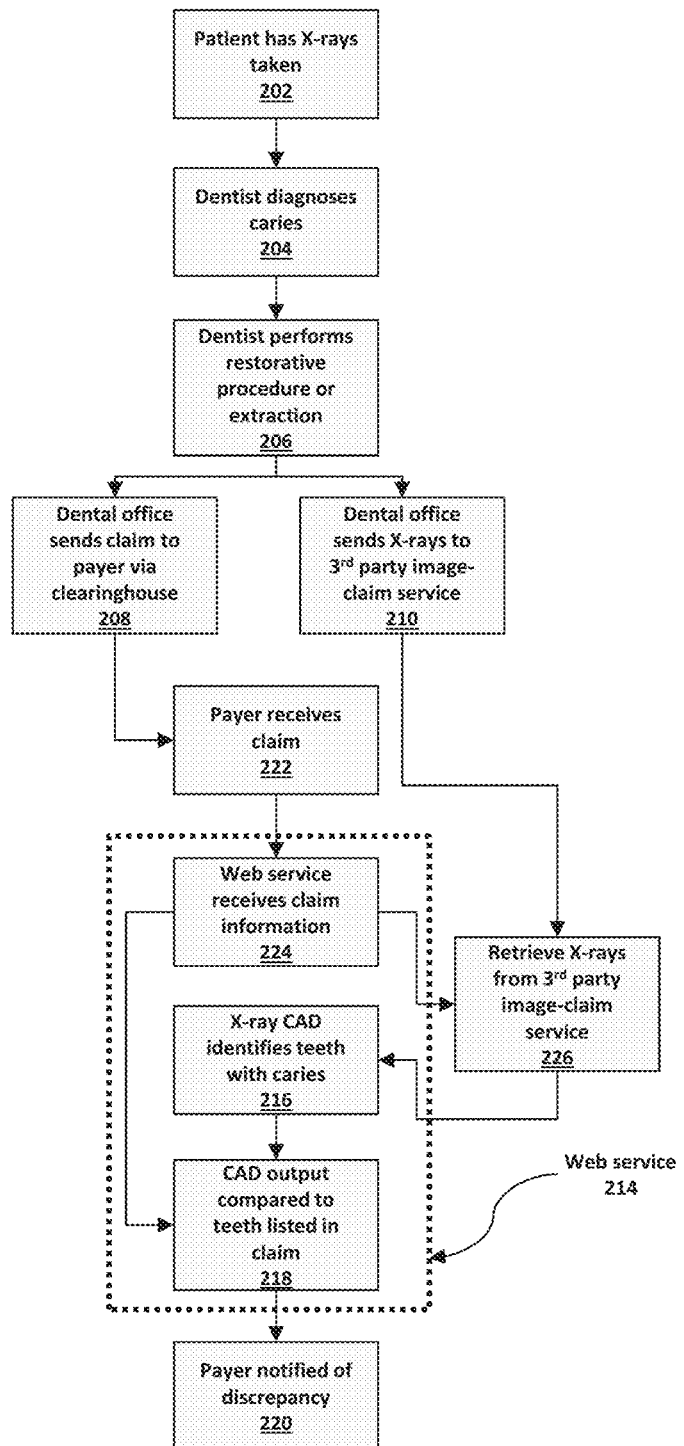
FIG. 2B is an alternate embodiment of the flowchart shown in FIG. 2A.

FIG. 2A is a flowchart illustrating one of the embodiments of the process, starting from when a patient has X-rays taken at an office appointment to the Payer being notified of a discrepancy between pathology on the X-ray and the reimbursement claim. Consider the case where a patient visited a dentist, has an X-ray taken (Step 202), the dentist "found a cavity (caries)" (Step 204), and put in a filling (Step 206). After the patient's visit has concluded, the dental practice electronically sends the Payer an EDI 837 claims file (Step 208). This 837 file indicates, among other things, a procedure code for the restorative procedure and the tooth number and surface(s) that were treated. Because the Payer requires documentation for this procedure, the dental office transmits X-ray images that show the decay in the treated tooth (Step 210). NEA FastAttach™ is the third-party image-claims attachment service that is most widely used in the United States. In the illustrated embodiment, prior to the Payer's claims processing agent reviewing the claim, once the Payer receives both the EDI 837 claim and the X-rays (Step 212), the Payer's claims management system transmits the 837 file or the portion thereof that relates to the patient in question and the X-ray image file to a web service 214 to perform CAD (Step 216) and comparison (Step 218). The web service 214 responds with an indication of whether the decay that was the reason for the restoration was (or was not) detected in the image (Step 220). Having received the CAD analysis, the claims agent of the Payer can assess whether to process or deny the claim. Note that in one alternative embodiment, the web service 214 is utilized by the third-party image-claim attachment service. FIG. 2B illustrates another alternate embodiment, where the exam images are retrieved by the web service (Step 224). This embodiment does not need the images to be sent by the Payer because the 837 file contains the NEA FastAttach™ ID corresponding to the exam. Consequently, with proper permissions, the web service can retrieve the images directly from NEA FastAttach™. The Payer, in this embodiment, receives only the claim 222. The claim is sent to the web service 214, which retrieves the images from the third-party image-claim service (step 226). The CAD identifies teeth with caries 216, the results are compared to the information in the claim 218, and the Payer is notified of a discrepancy or agreement.

Figure 3:
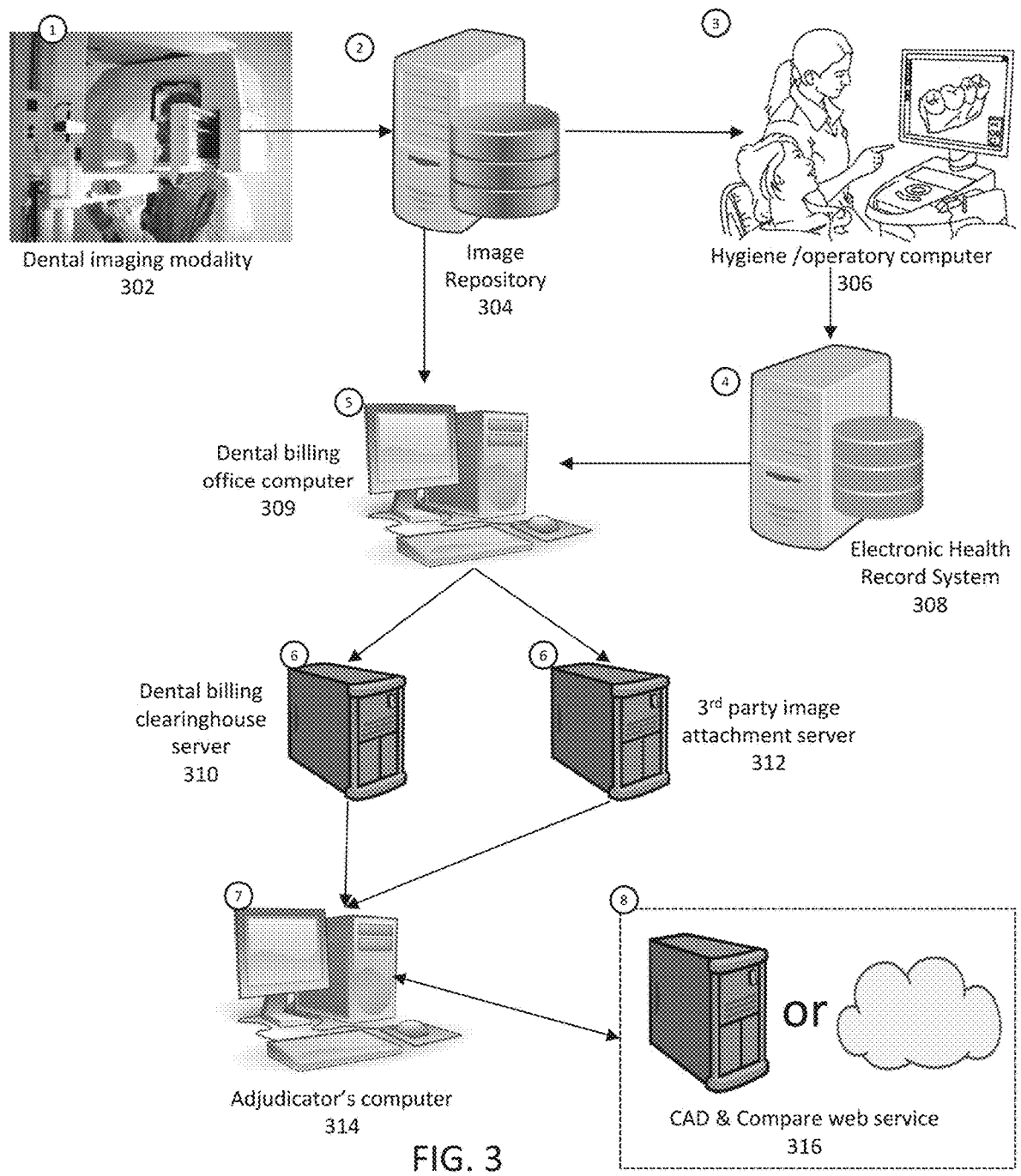
FIG. 3 is a block diagram showing connections between hardware devices in one embodiment.

FIG. 3 is a block diagram showing connections between hardware devices in one embodiment. In FIG. 3, images are acquired by a dental imaging modality 302. The dental imaging modality 302 may be a computed- or digital-radiography system, intraoral camera, a panoramic X-ray, a cone-beam CT scanner, and the like. The images from the dental imaging modality 302 are saved in an image repository 304, which could be either on-premises or cloud-based. A dentist or other health professional reviews the images on a computer 306 in the dental office, typically in a hygiene room. A diagnosis and treatment plan are entered into an electronic health record system 308 on a computer in the dental office, typically in a hygiene room or operatory. This may be the same computer or a different one as the computer 306 used to review the images. A member of the dental office's staff prepares a claim from an office computer 309. (Again, this may be the same computer or a different one as the computer 306 used to review the images.) The office staff person sends the claim to a claims processing clearinghouse 310 and sends the images to a third-party claims attachment service 312. A claims adjudicator working for the Payer will receive the claim and images on an adjudicator's computer 314. The claim and images are sent to a web service 316 for CAD of dental caries and a comparison against the claim, as described herein. The web service 316 returns a notice of whether the claim and images agree, or a description of the discrepancy.

Figure 4:
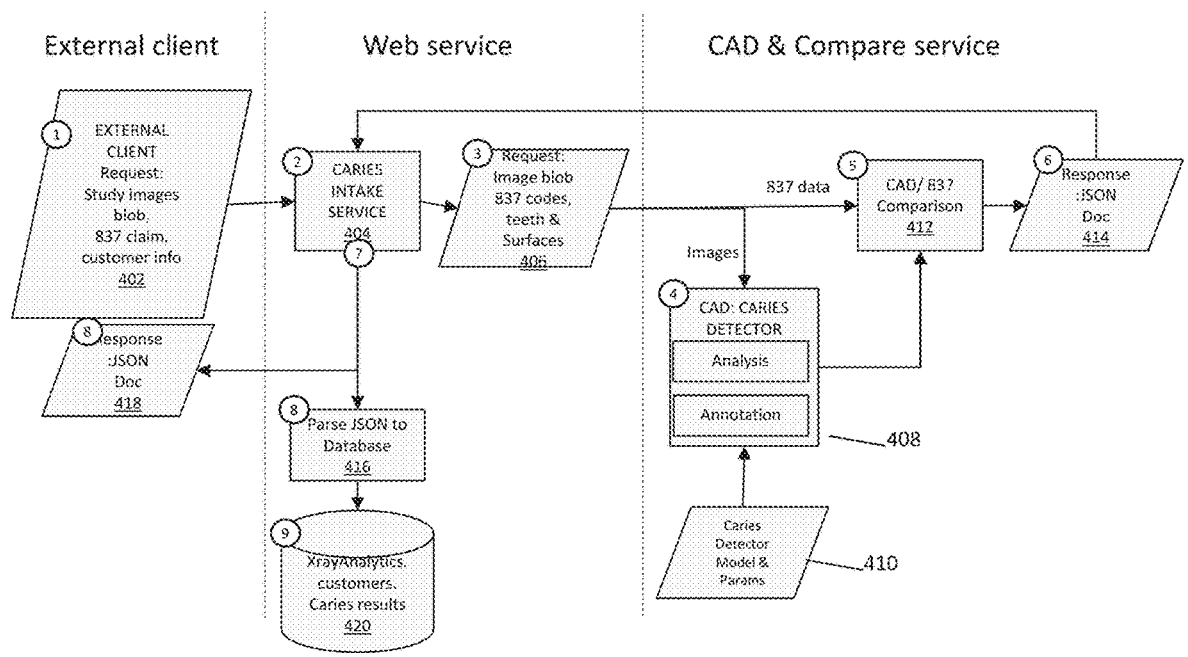
FIG. 4 is a flowchart that illustrates how the web service (from FIG. 2, FIG. 3, or both) works.

FIG. 4 is a flowchart that illustrates how the web service (from FIG. 2, FIG. 3, or both) works. At 402, an external client, such as a Payer's claims processing system, requests an analysis from the service. The request includes, for example, sending the 837 file or the set of procedure attributes, the X-ray images (sent as a "blob"), and information identifying the Payer as a customer of the service. This is to allow only the most relevant information from the 837 file to be sent, so that the system never has to touch Protected Health Information that is not needed for the CAD/CADx. At 404, an intake service parses the 837 file to identify relevant procedures, teeth, and surfaces, and passes that information (step 406), along with the images, as a request to a second service to perform the CAD and comparison. At 408, the caries detector CAD process evaluates one image a time. At 410, the CAD software receives a configuration of the caries classifier (106). For example, the graph, weights, and biases of a CNN. At 412, the output of the CAD, a list of teeth and surfaces with caries, is compared against the list parsed from the 837 file. At 414, the second service sends a JSON response to the first service (step 404), indicating whether there is agreement or specifying the discrepancy between the lists. At 416, this first service saves the results to a database 420 and at 418 sends an agreement/discrepancy response back to the external client that initiated the transaction. It is to be appreciated that the services described here may run on one or more physical servers that may or may not be located in close proximity.

Figure 5:
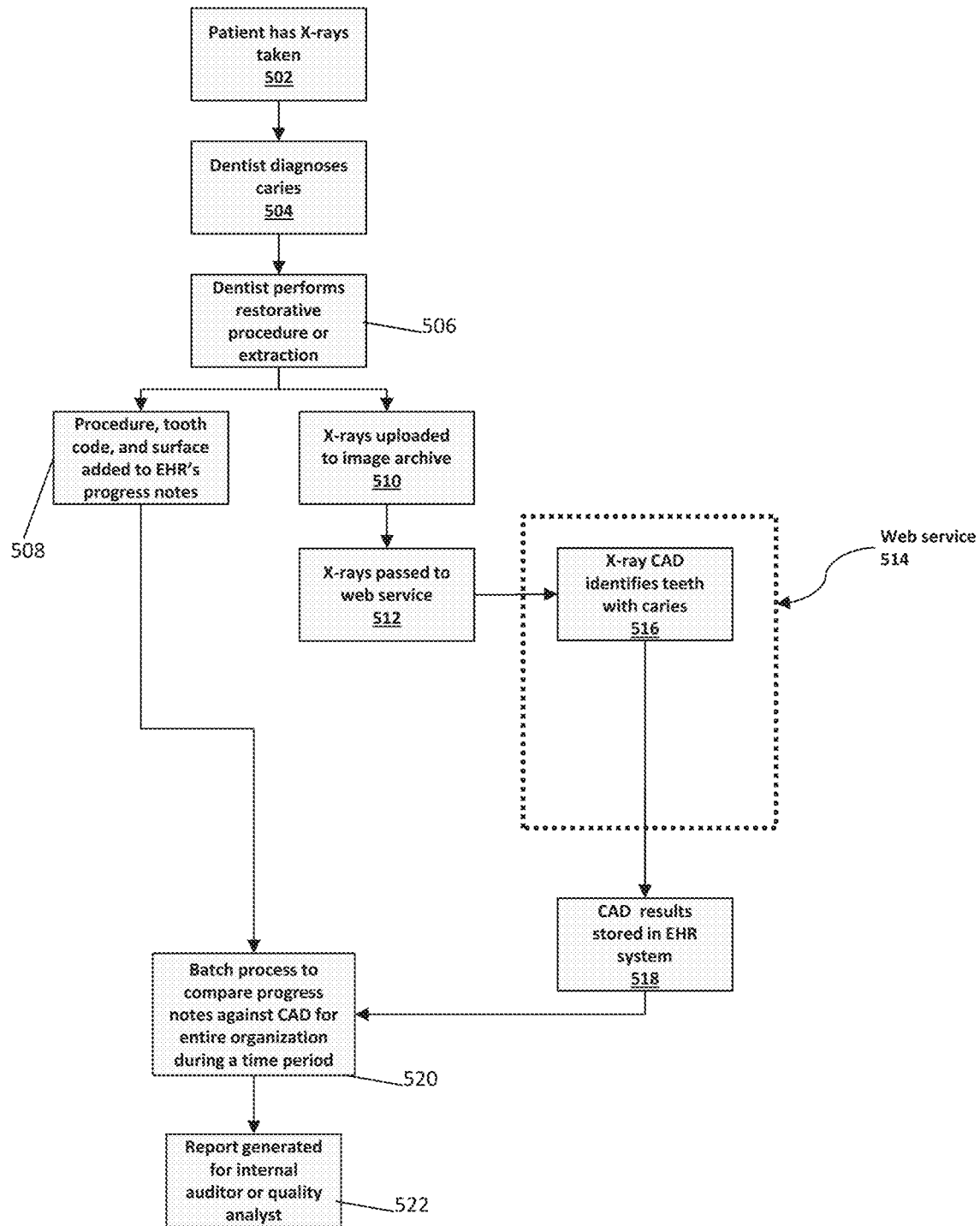
FIG. 5 is a flowchart that illustrates an "internal auditing" aspect of embodiments of the invention.

FIG. 5 is a flowchart that illustrates an "internal auditing" aspect of embodiments of the invention. As shown in FIG. 5, at 502 a patient has X-rays taken of one or more teeth. At 504, a dentist, using experience and training, makes an assessment using both the X-rays and an inspection of the patient's teeth, determines whether the patient has one or more caries. The dentist then proceeds to perform a restorative procedure or extraction on the one or more teeth identified with caries, at 506. At 508, relevant procedures, teeth, and surfaces for the patient are included in an electronic health record (EHR). The record of the restorations, extractions, or both is entered in the progress notes of an electronic health record of the patient. ("Progress notes" is a term in the medical field meaning the record of what the healthcare provider has observed and performed.) At 510, the X-rays are transmitted to an image archive, where (at 512) they are passed to a web service 514. For example, the X-ray images may be uploaded to an enterprise-level image archive, such as a Picture Archive and Communications System (PACS). In the web service 514, at 516 the X-rays are analyzed using CAD (as described herein) to identify any teeth with caries. At 518, the output of the CAD analyses (i.e., the CAD results) are stored in the EHR system. At 520, a batch process is executed that compares (on a one-to-one basis) the EHR's notes for a patient (i.e., the dentist's diagnoses) with the CAD analysis for the same patient. This comparison can be conducted for all patients over a defined period of time, a select number of patients over a period of time, and the like. The comparison of the dentist's diagnosis to images can be performed without producing an 837 claim file. During the comparison, the server queries the EHR system for new progress notes that indicate a procedure that was based on a dentist's interpretation of radiographs; for example, a composite restoration on the distal and occlusal surfaces of a given tooth The comparison batch process is executed to compile into a report on the diagnostic performance statistics for one, a select group, or all the dentists in a dental organization. This process queries the EHR's CAD records for all instances of patients who had computer-detected caries in their X-rays, queries the EHR system for instances of progress notes with restorative procedures (e.g., CDT code D2331, resin-based composite, two-surface restoration), and makes a comparison of the two.

Figure 6:
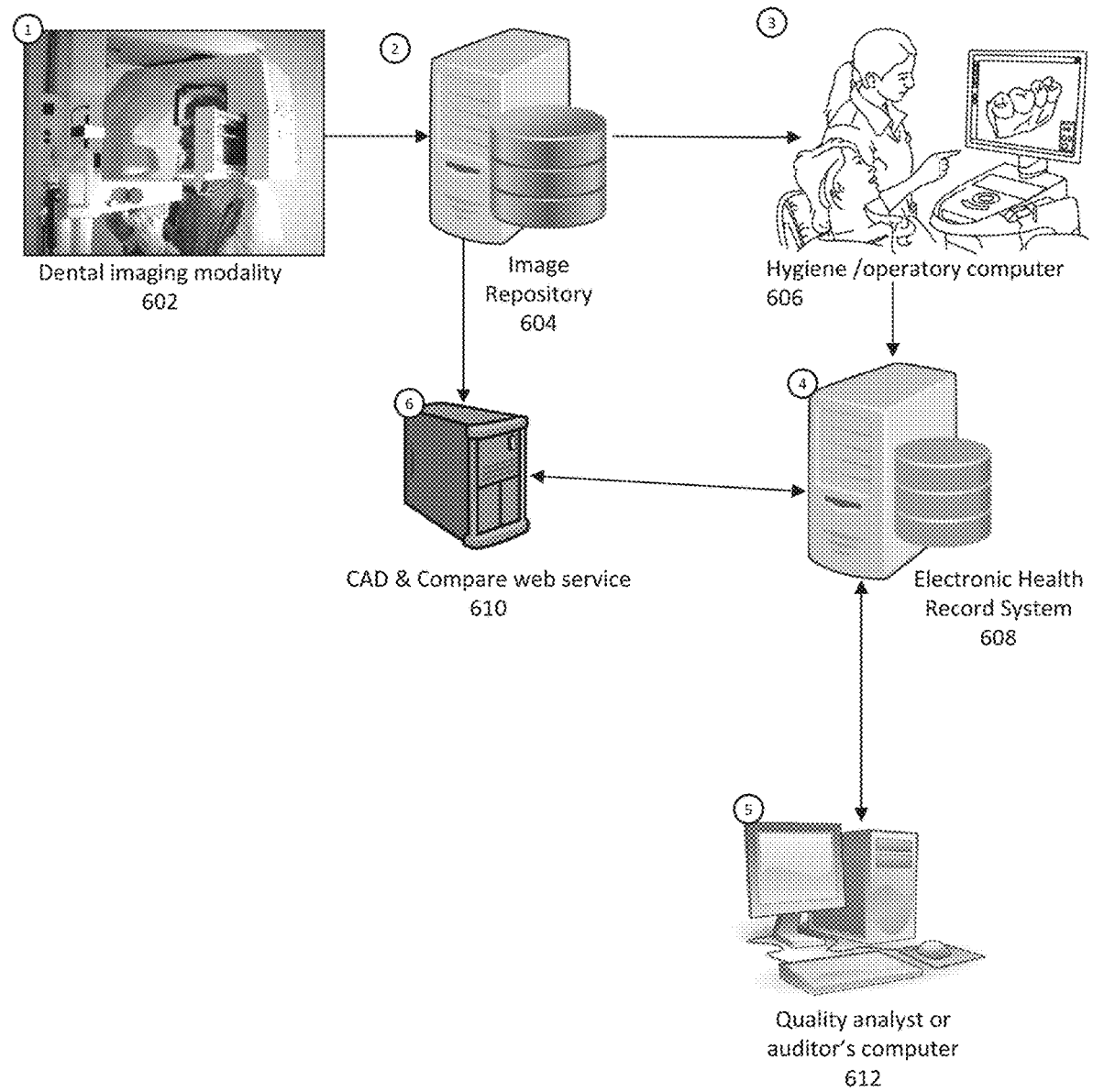
FIG. 6 is a block diagram showing an example of connections between hardware devices in the internal auditing embodiment.

FIG. 6 is a block diagram showing an example of connections between hardware devices in the internal auditing embodiment, as described above. In this example, the dental imaging modality 602 may be, for example, a computed- or digital radiography system, intraoral camera, a panoramic X-ray, a cone-beam CT scanner, and the like. The images from the modality are saved in an image repository 604, which could be either on-premises, in a data center, or in the cloud. A dentist reviews the images on a computer 606 in the dental office, typically in a hygiene room. A diagnosis and treatment plan are entered into an electronic health record system 608 on a computer in the dental office, typically in a hygiene room or operatory (which may, or may not, be the same as computer 606). On a per-case or in a batch process in a group on a periodic basis, a process in the electronic health record system 608 sends images and diagnosis codes to the CAD-and-compare web service 610, which returns an indication of whether the two agree. The practice management service (EHR) 608 also compiles the performance metrics for the dentists in the organization and prepares a report for viewing and analysis by a quality analyst or auditor 612. The quality analyst or auditor may use the same or a different computer as computer 606 in the dental office.

Figure 7:
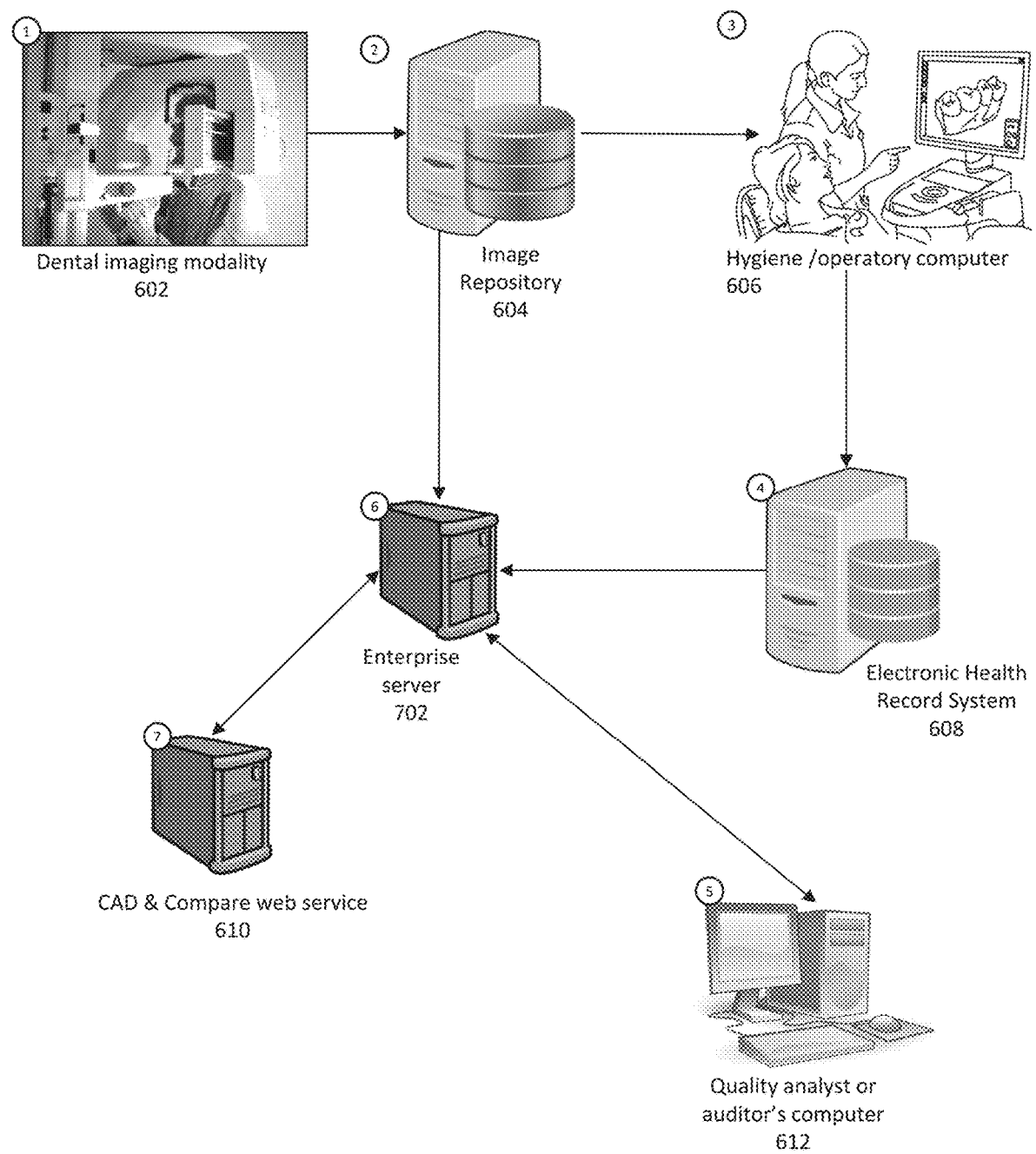
FIG. 7 shows a variation of the exemplary hardware arrangement shown in FIG. 6.

FIG. 7 shows a variation of the exemplary hardware arrangement shown in FIG. 6. In FIG. 7 there is a separate, enterprise-related server 702 that is an intermediary between the image repository 604, electronic health record system 608, and the CAD-and-compare web service 610. On a per-case or in a batch process in a group on a periodic basis, a process on the enterprise server 702 sends images from the image repository 604 and diagnosis codes from the electronic health record system 608 to the CAD-and-compare web service 610, which returns an indication of whether the two agree. The enterprise server 702 also compiles the performance metrics for the dentists in the organization and prepares a report for viewing and analysis on a computer by a quality analyst or auditor. The quality analyst or auditor may use the same or a different computer as computer 606 in the dental office.

Figure 8A:
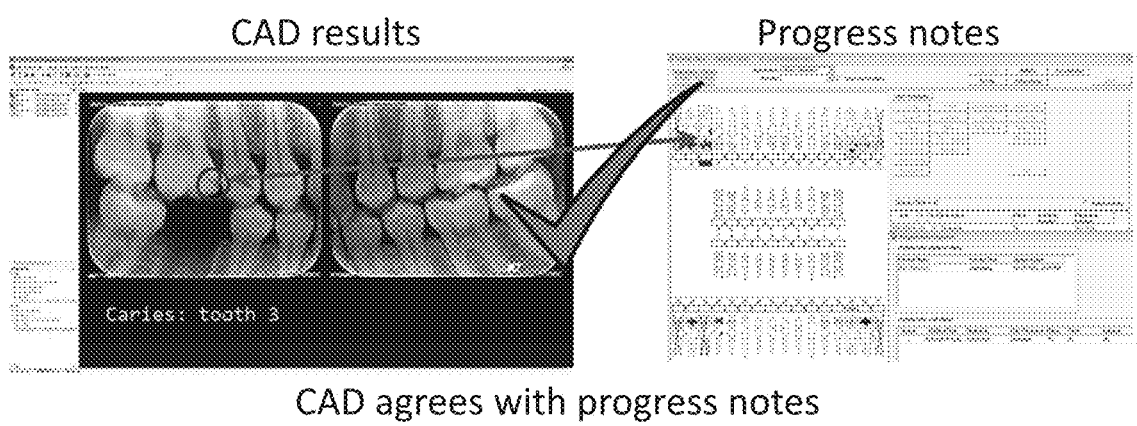
FIGS. 8A and 8B illustrate two cases of comparison between the CAD results and the progress notes.
Figure 8B:
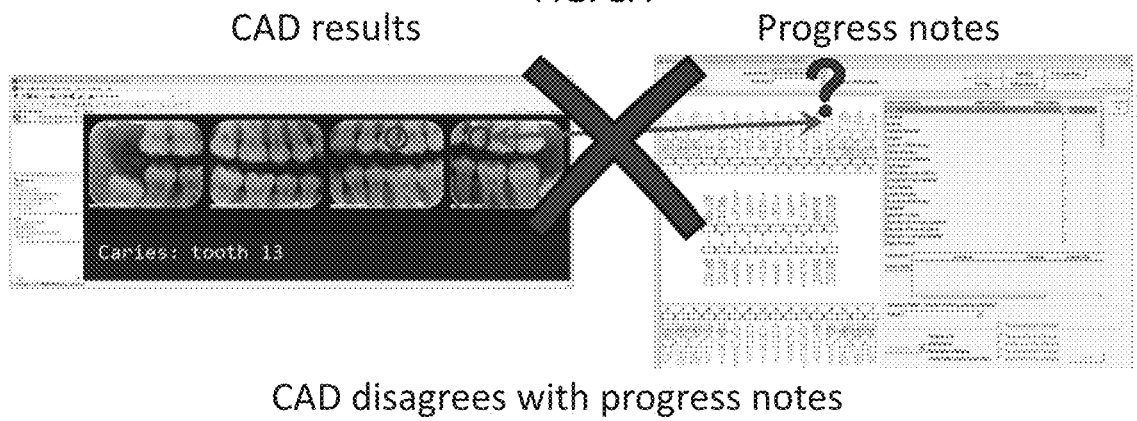

FIGS. 8A and 8B illustrate two cases of comparison between the CAD results and the progress notes. In the first example, FIG. 8A, the CAD results indicate caries on tooth 3, as indicated by the circled area on the X-ray. The dentist's progress notes indicated a restoration on tooth 3. The comparison process counts this case as a CAD-progress notes agreement. In the second example (FIG. 8B), the CAD service detected caries on tooth 13 (circled); however, the progress notes from the corresponding patient visit do not indicate either a restorative procedure or extraction having been performed or planned. In this case, the process will count this case as a CAD-progress notes disagreement.

Figure 9:
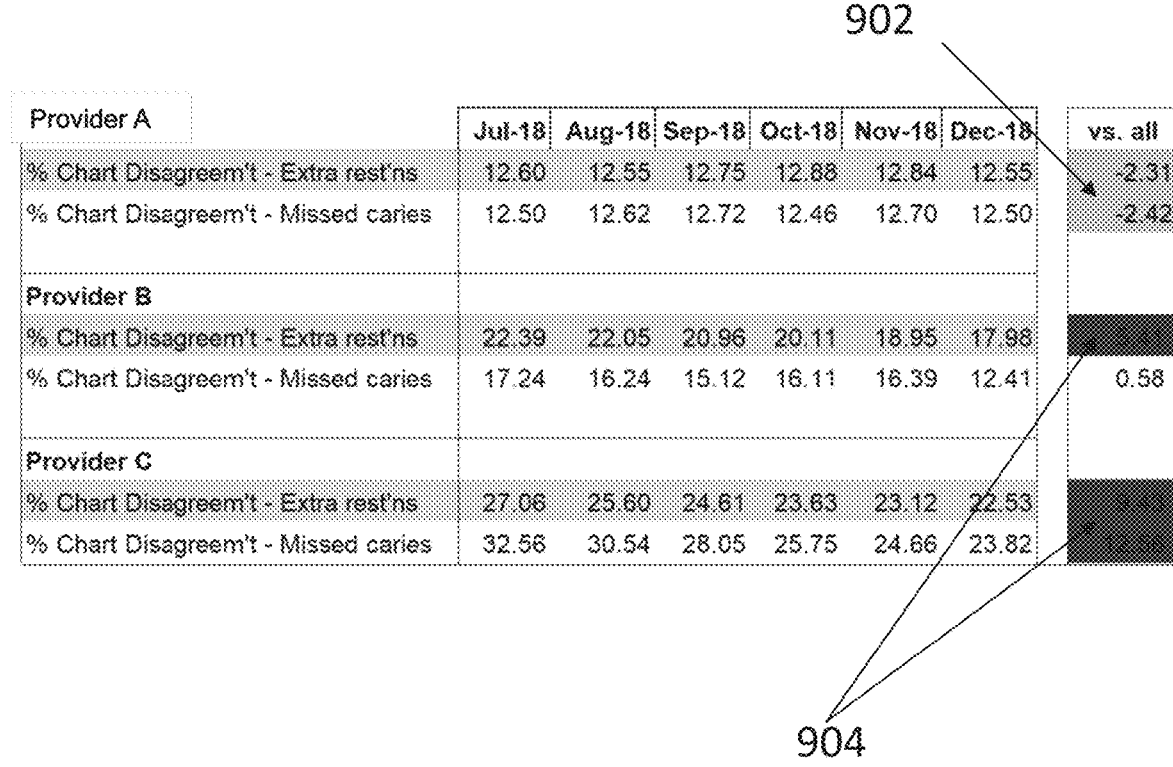
FIG. 9 illustrates an exemplary report generated by the batch process described above.

FIG. 9 illustrates an exemplary report generated by the batch process described above. For each provider (e.g., dentist), the batch process tallies the frequency of caries not being diagnosed and the frequency of caries being diagnosed without CAD detection of decay. An auditor or quality analyst can review the report to identify dentists whose diagnostic skills are below the norm and direct that dentist for additional radiography training. In the figure, the last column has color-coding to indicate which dentists diagnose significantly better than the group (shaded green 902) or significantly worse than the group (shaded red 904).

Figure 10:
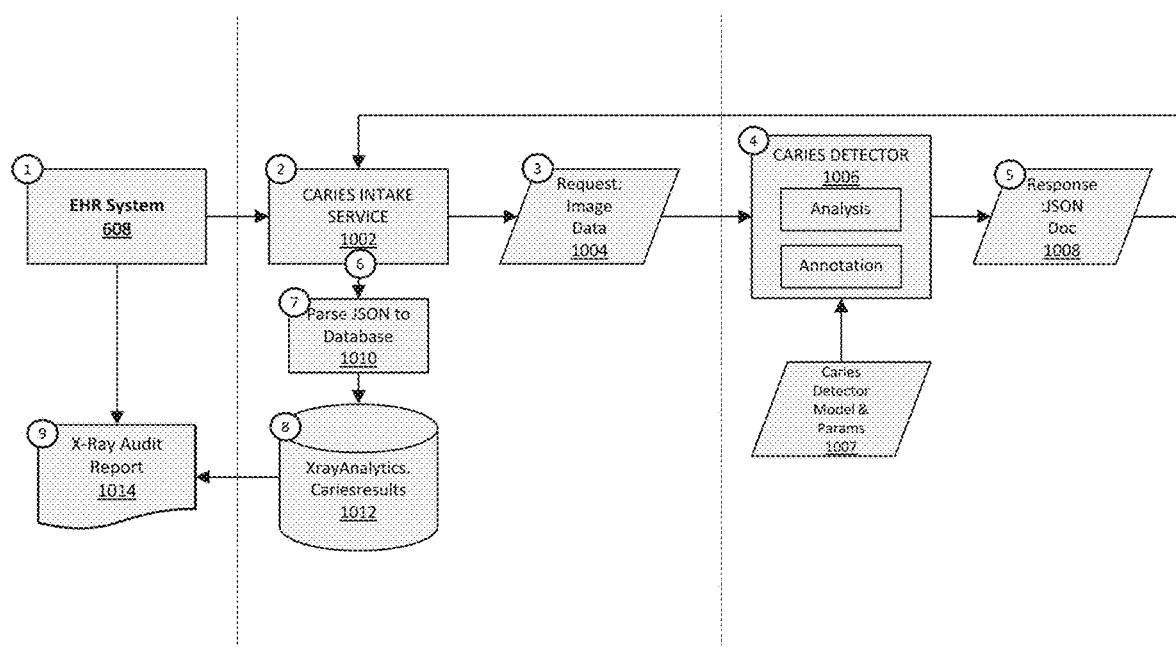
FIG. 10 is a chart that shows additional detail of the internal auditing embodiment to facilitate the production of audit reports.

FIG. 10 is a chart that shows additional detail of the internal auditing embodiment to facilitate the production of audit reports. An intake service 1002 monitors the EHR 608 for records of new radiographs having been acquired and sends copies of the images 1004 to a CAD service 1006. The CAD service 1006 performs the caries detection (using a caries detector model 1007) and responds with a JSON document 1008 containing list of teeth with caries to the intake service 1002. The intake service 1002 parses this document 1010 and stores the CAD results in a database 1012. The database record stores, among other things, a patient identifier and a provider identifier. The X-ray audit report 1014 pulls records from the CAD service 1006 and the progress notes in the EHR 608.

Figure 11:
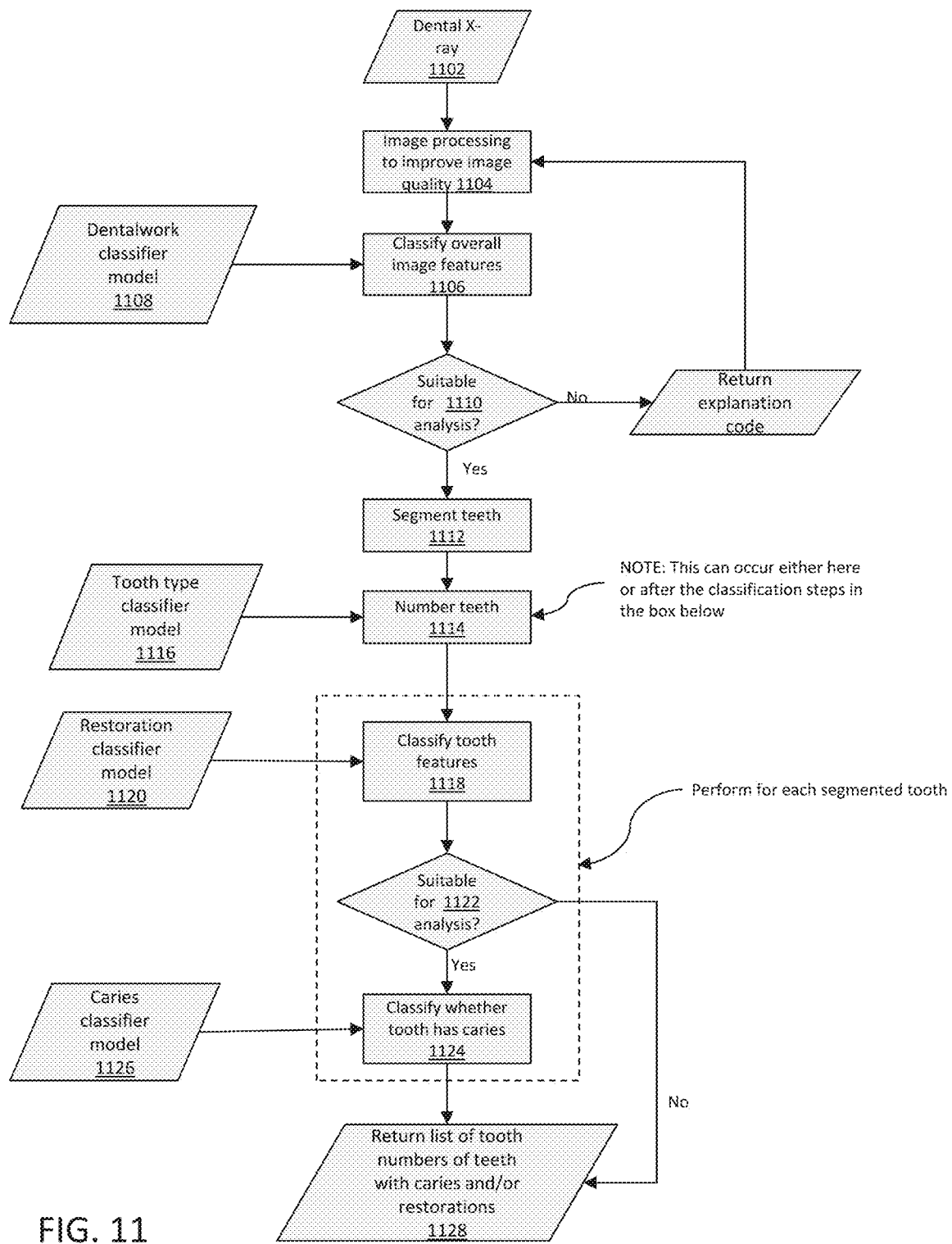
FIG. 11 is a flowchart illustrating CAD for detecting caries.

FIG. 11 is a flowchart illustrating CAD for detecting caries. The process is generally comprised of three steps: segmenting teeth from an X-ray showing multiple teeth, numbering the segmented teeth, and classifying the segmented teeth as having caries or not. The second and third steps may be performed in any order, however, if the numbering occurs first, it permits the use of multiple image classifiers that were trained to be used specifically for one type of tooth (e.g., primary molars or secondary premolars).

The process starts at 1102, obtaining an X-ray. An optional step, image processing 1104, to improve the quality of the X-ray image may occur. Generally, image processing starts by using homomorphic filtering on the image to normalize the range of image intensity throughout the image. It is common for the teeth on one side of an X-ray to be brighter than those on the other side. Homomorphic filtering corrects for this phenomenon. Any bright white areas around the border of the image, caused by phosphor-plate reader artifacts, for example, are set to a zero intensity. Also, optionally, the X-ray image may undergo classification of overall image features 1106, using a classifier model 1108. The classifier model 1108 comprises an image classifier that is trained to identify X-rays that include orthodontia or images that are of poor quality; it is used to determine whether the image is suitable for analysis. In one aspect, the classifier is a CNN (Convolutional Neural Network) using the AlexNet architecture. (Note that there are many CNN architectures that are well-suited to image classification, GoogleNet for example. Any of these architectures could be used.) At 1110 it is determined, using the image classifier, whether the image is suitable for analysis. If not, a return explanation code is provided, and the image may undergo additional image processing 1104 or the image may be discarded. If, at 1110, it is determined that the image is suitable for continued CAD, then the process goes to 1112. At 1112, if the image is comprised of a plurality of teeth, each tooth is individually segmented, (shown in detail in FIG. 12) to determine boundaries between teeth.

Figures 13A, 13B, 13C, 13D, 13E:
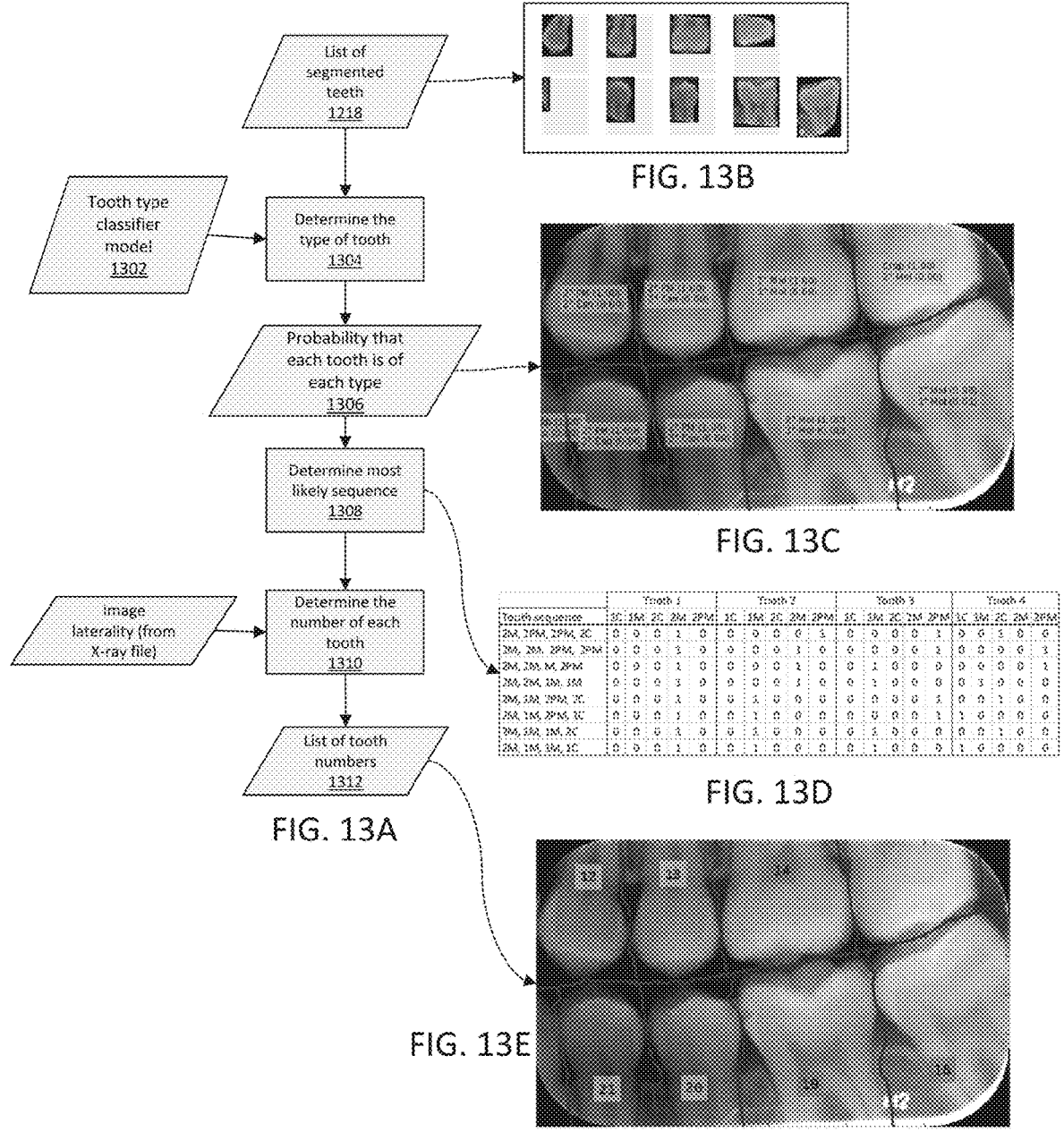
FIG. 13A is a flowchart that shows a process by which teeth are numbered according to the Universal Numbering System.
FIGS. 13B-13E are illustrations associated with the flowchart of FIG. 13A.

Once the image undergoes segmentation (1112), each of the segmented teeth are numbered at 1114, using a tooth-type classifier model 1116. This is explained in greater detail with reference to FIG. 13A. FIG. 13A shows the process by which teeth are numbered according to the Universal Numbering System. The result is that each tooth is assigned a number from 1-32 (adult teeth) or letter from A-T (deciduous teeth), which can be corresponded to information in the patient's progress notes. Alternatively, the teeth can be numbered according to the ISO 3950 notation.

Once segmented and numbered, each tooth image undergoes a CAD analysis, which is explained in even greater detail with reference to FIG. 14. Each tooth image undergoes CAD for (optionally) restoration 1118, using a restoration classifier model 1120, and caries 1124, using a caries classifier model 1126. The restoration image classifier determines whether there are any other features that may produce erroneous results by the caries classifier. In this embodiment, a restoration detector identifies teeth with restorations that may produce false negative results from the caries classifier. This step is helpful, but not necessary. A caries classifier trained on enough teeth with restorations may be robust enough to not need a restoration classifier. Optionally, there may be a step (1122) between restoration analysis 1118 and caries analysis to determine whether a tooth identified as restored is suitable to undergo caries analysis 1124. If the tooth, at 1122, is identified as suitable for analysis, then it undergoes caries analysis at 1124. If the tooth is suitable for caries classification, it is classified as having caries or not by using a CNN specifically trained to determine whether a tooth has caries. In this embodiment, the GoogLeNet architecture may be used. The output of this classification step, along with those from the other teeth in the X-ray, is returned to the requesting service. If, at 1122, it is determined that the tooth is not suitable for caries analysis, then at 1128 it is added to a list of teeth that have undergone restoration. After CAD analysis, at 1128 a list of tooth numbers with caries and/or restorations is returned.

FIG. 12A is a flowchart illustrating a tooth segmentation algorithm. A first step in this process is to obtain an x-ray image 1202. At 1204, the x-ray image is examined to separate the upper teeth from the lower teeth by identifying the occlusal plane. The occlusal plane (or in this case, a curve) is the separation between the upper teeth and the lower teeth. Each half (upper/lower) is segmented independently, though the process for only the upper teeth 1206 is described in this flowchart. In one aspect, the occlusal plane is identified by rotating the image several degrees in the clockwise and counterclockwise direction, where at each increment a projection of intensity for each image row is summed. The occlusal plane is identifiable by a valley in the profiles of this projection ("occlusal valley"). The angle for which the occlusal valley depth is maximized is selected as the orientation in which the occlusal plane lies. A further refinement of the occlusal plane is performed by examining each column (or several adjacent columns) in the rotated image, identifying the row corresponding to the maximum depth of the occlusal valley in that column (or group of adjacent columns). The occlusal curve is a smoothed curve of these maximum valley depth locations spanned along the rows of the image.

The boundaries between each tooth, determined independently for the upper or lower set of teeth, are constructed by taking a column-wise projection of intensities between the occlusal curve and the edge of the image (step 1208). FIG. 12B illustrates these curves. The spaces between the teeth are indicated by the valleys in the projections. A more refined location can be obtained by (step 1210) again rotating the image a few degrees and (step 1212) making note of the columns on which the valleys bottom out for all the rotations. K-means may be used to determine a good average position of the columns that roughly separate the teeth. This list of column locations will be used as starting points to more precisely segment the teeth from each other.

For each column location found in the previous step, a rectangular window is incrementally moved from the occlusal curve towards the edge of the image, as shown in FIG. 12C. The tooth segmentation line is chosen to be at the column of this window for which the average intensity in the window is the minimum. The set of column and window center-row coordinates is smoothed to produce a curve separating the teeth to the left and right of the curve. However, these curves are prone to inadvertently running through a tooth because the pulp inside each tooth is dark, which can create a "false valley" in the column-wise projections. To filter these curves out, at step 1214 the image intensity along that curve is compared to those of curves translated to the left and right of the segmentation curve (see FIG. 12D). Segmentation curves that run through the pulp of a tooth will have more similar intensities to each other, compared to a segmentation curve that runs between the teeth. Curves for which the intensities are too close to each other are rejected. When all the segmentation curves are put together (step 1216), the image is segmented as shown in FIG. 12E. At step 1216, the output of the segmentation process 1218 is a set of small images, as shown in FIG. 12F-one for each segmented region. Optionally, the small images from the upper arch are flipped about a horizontal axis so that the occlusal surface of the tooth is towards the top part of the image. The motivation for that step is that the classifiers can be more effectively trained if the tooth orientations are the same for all the images on which it is trained.

FIG. 13A illustrates one fuzzy-logic process by which the teeth can be numbered. From the output of the segmentation process 1218 and its set of small images (FIG. 13B), a tooth-type classifier 1302 identifies, at step 1304, the likelihood that the segmented tooth image contains any of several types of tooth. These may be primary molars, secondary molars, primary canines, secondary canines, secondary premolars, primary incisors, secondary incisors, gaps between teeth, exfoliating teeth, and cropped teeth. At 1306, the probabilities of tooth types for the teeth are arranged in a list of length number of teeth X (multiplied by) number of tooth types. FIG. 13C shows an X-ray labeled with the top two most likely tooth types for each segmented tooth.

Note that there are a limited number of permutations of tooth type that can exist, so the most likely sequence is determined (step 1308). Some permutations of 4-tooth sequences (from back of mouth to front) are shown on the leftmost column of FIG. 13D. The right-hand side of FIG. 13D is a matrix whereby each row is a list of the same length and order of the tooth type list, but the values are all zeros except in the place for a particular tooth type, where they are ones. The tooth probability list is element-wise multiplied against each row of the matrix and the products summed to produce a sequence score (step 1310). At 1312, the tooth labeling is determined by the row with the highest score. An example of the output of this step is shown in FIG. 13E.

Figures 14A, 14B, 14C, 14D, 14E:
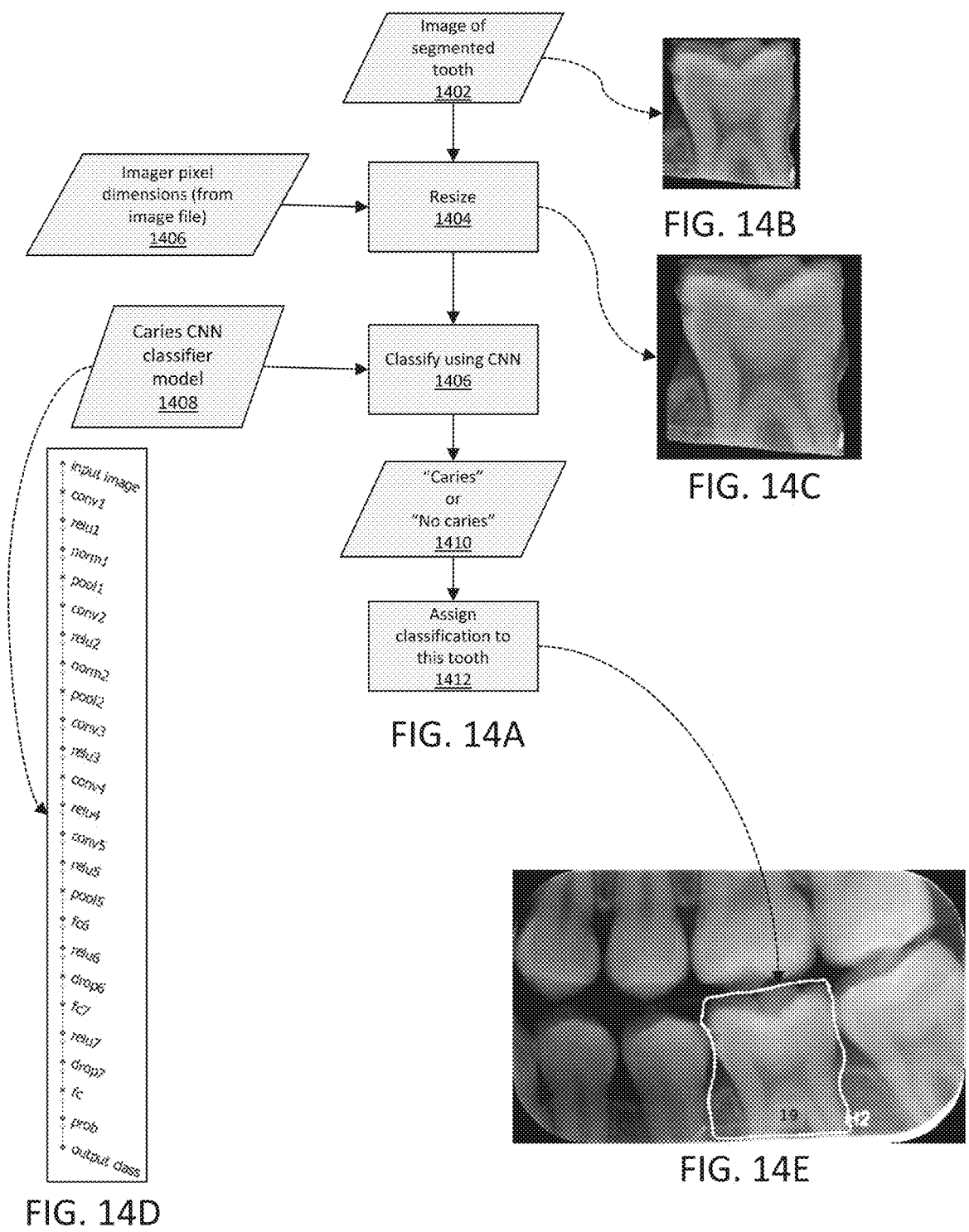
FIG. 14A is a flowchart that illustrates how convolutional neural network (CNN)-based image classifiers are applied.
FIGS. 14B-14E are illustrations associated with the flowchart of FIG. 14A.

As been previously mentioned in this description, CNN-based image classifiers are used in several places to determine the content of an image. FIG. 14A is a flowchart that illustrates how these classifiers are applied. Starting (step 1402) with a segmented tooth image (or, in the case of the orthodontia classifier, the whole X-ray image), FIG. 14B, the image is scaled (step 1404, FIG. 14C) to the dimensions required by the particular CNN model. For example, 224× 224×3 pixels. Although the X-rays are grayscale, the CNN models used in these embodiments were designed for RGB images. Consequently, the scaled images have three channels. For the segmented teeth, the scaling takes into account the physical dimensions of the image sensor to preserve the relative physical dimensions of a tooth relative to any other. The scaling is based on the physical imager size 1406, which is a parameter embedded in the metadata of the X-ray image file.

The scaled image is passed into a CNN at 1406. The CNN classifier model's architecture, weights, and biases have been pre-determined by a machine learning training session (1408). The graph of the AlexNet architecture is shown in FIG. 14D. The output (1410) of the classifier is a binary output: "has caries" or "does not have caries." This result, along with the tooth number, is the output of the CAD classifier process (1412). In one aspect, the output can be visualized to assist a clinician by putting an identifier in the image such as, for example, a circle around caries or tracing a circle around the tooth with caries, as shown in FIG. 14E.

Figure 15:
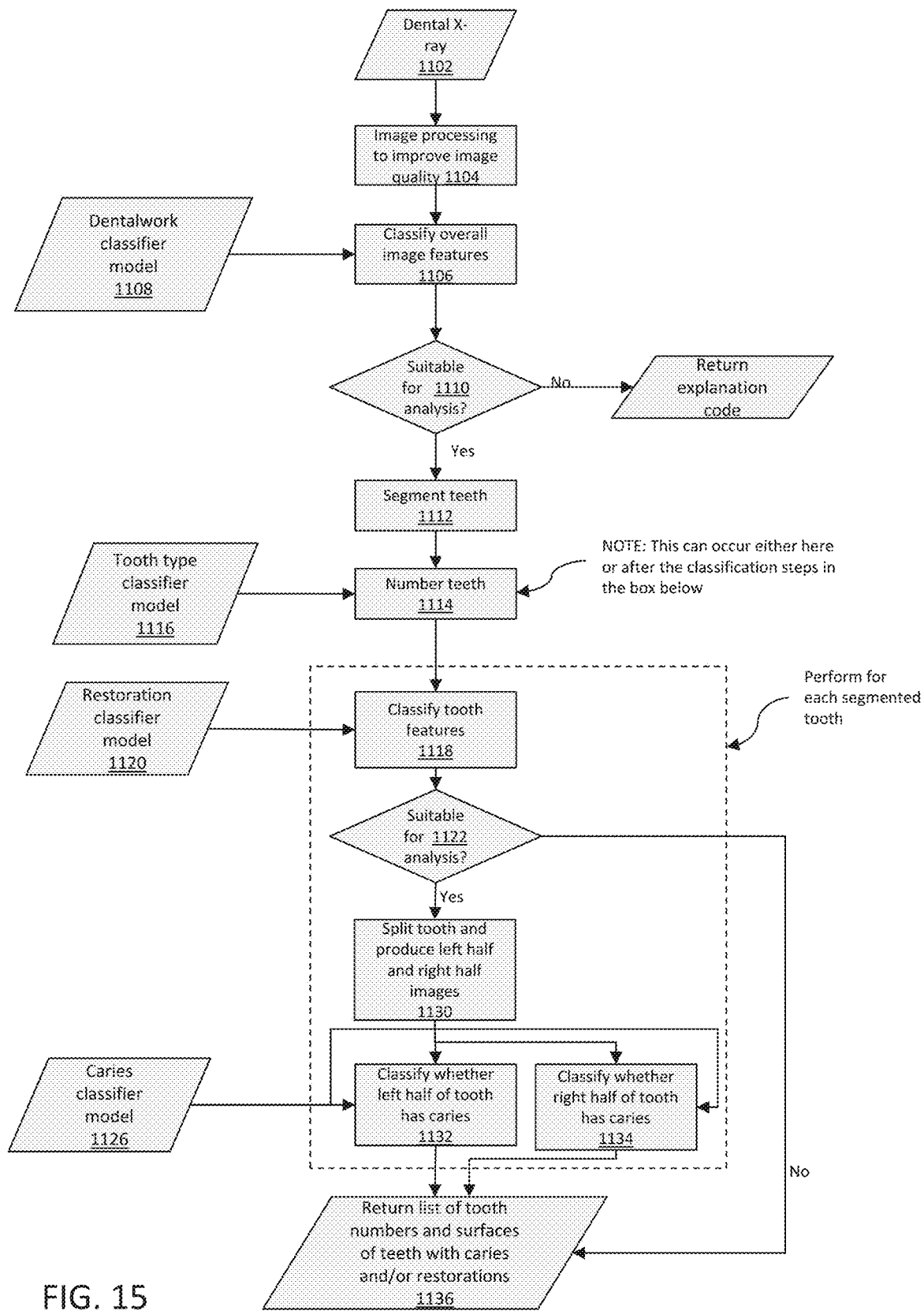
FIG. 15 is a flowchart illustrating CAD for detecting caries where the left and right halves of the tooth are separately classified.
Figure 16A:
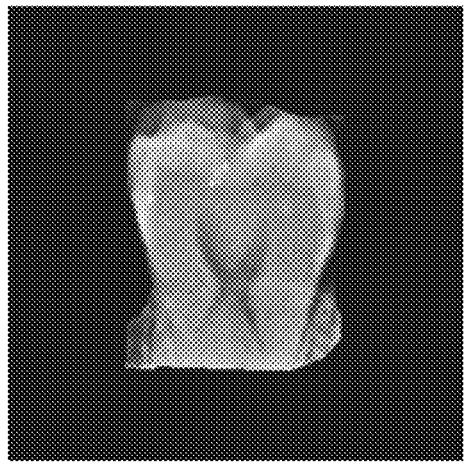
FIGS. 16A-16C are illustrations of how a segmented tooth image is split into left and right half images.
Figure 16B:
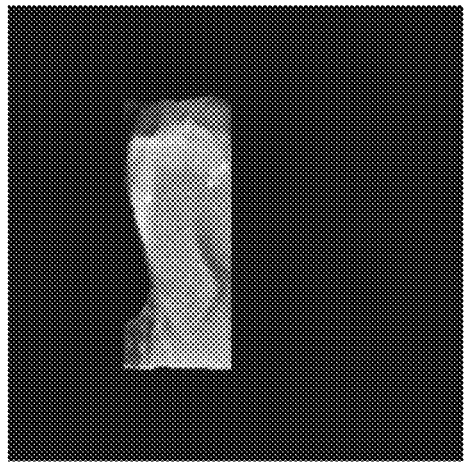
Figure 16C:
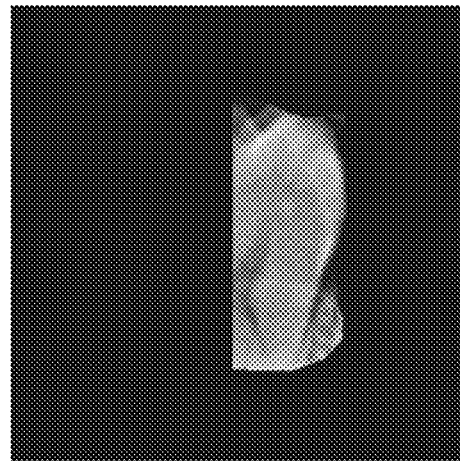

FIG. 15 is a flowchart illustrating CAD for detecting caries where the left and right halves of the tooth are separately classified. In this embodiment, after step 1122 (see FIG. 11, above), at 1130 the segmented tooth image is split into an image containing the left half of the tooth and an image containing the right half of the tooth (see FIGS. 16A-16C for illustrations). As an example, the first mandibular molar in a bitewing X-ray of the patient's right-hand side would be split into a distal half (left image) and mesial half (right image). The tooth image is first rotated by the amount that would transform the occlusal plane (from step 1204) to lie in a horizontal orientation. The tooth is then split along a vertical line that bisects the tooth. In cases where half of the tooth was already cropped in the radiograph, the cropped portion of the tooth is not split.

The left side images are flipped about a vertical axis so that the proximal surface of the tooth is on the right side of the image. This is performed so that the orientation of the half-teeth is the same for both left and right images. The motivation for this step is that the caries analyzer can be more effectively trained if the surface orientations are the same for all the images on which it is trained. Note that this flipping step is not mandatory.

The left and right images are classified by a caries classifier model (steps 1132 and 1134) as either having caries or being free of caries. If caries is detected, the tooth surface (mesial or distal) is determined by considering the laterality of the tooth (i.e., being on the patient's left side or right side) and whether caries was found in the left-half tooth image or right-half tooth image. After classification of all teeth is performed, at 1136 the system returns a list of tooth numbers and surfaces with caries.

Figure 17:
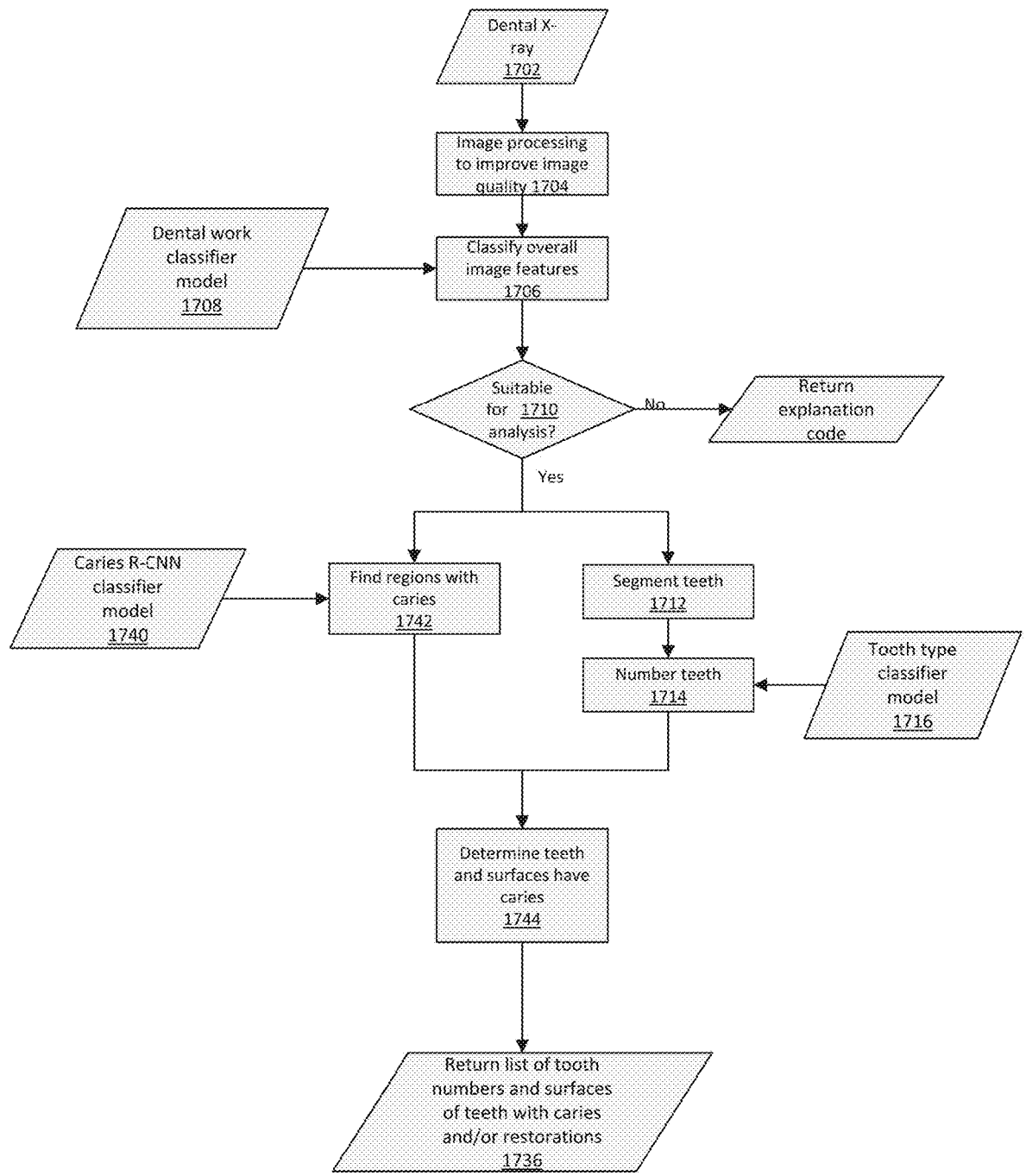
FIG. 17 is a flowchart illustrating CAD for detecting caries using a region-based convolutional neural network (R-CNN).

FIG. 17 is a flowchart illustrating CAD for detecting caries using a region-based convolutional neural network (R-CNN). An R-CNN 1740 detects objects in one or more positions in an image and returns a set of rectangular regions that contain an instance of the object. The embodiment using an R-CNN performs caries detection in the entire image at one step (step 1742), after determining whether the image is suitable for analysis. The R-CNN 1740 returns a list of rectangular regions with caries. It is still important to determine which teeth and surfaces have caries; this is accomplished (step 1744) by comparing the location of the rectangles in the image to the boundaries of the segmented and numbered teeth. The tooth surface—mesial, distal, occlusal, or a combination thereof—is assigned by determining where the bulk of the rectangle is with respect to the sides of the segmented tooth. Consider an example where the R-CNN returned a rectangular region containing caries that overlapped with the area in a segmented image containing tooth 31. If the rectangle is close to the right-hand side of the tooth 31 region in the segmented image, the surface that has caries is the mesial surface.

Figure 18:
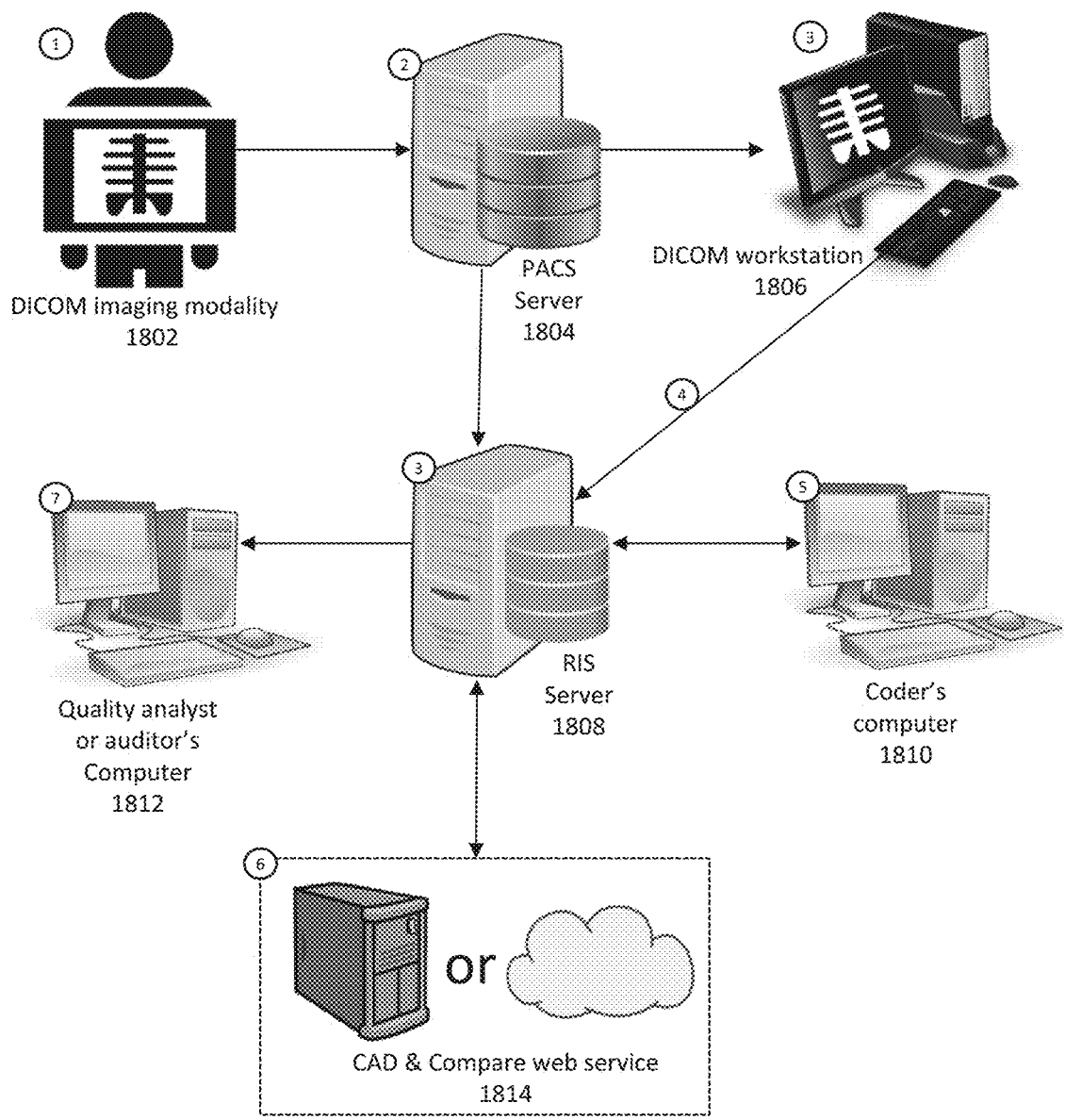
FIG. 18 is a block diagram showing the connections between hardware devices in an embodiment of CAD using non-dental medical images, in this example a radiology audit tool embodiment.

FIG. 18 is a block diagram showing the connections between hardware devices in an embodiment of CAD using non-dental medical images, in this example a radiology audit tool embodiment. The DICOM (Digital Imaging and Communications in Medicine) imaging modality 1802 that acquires the medical images in this embodiment can be, for example, computed- or digital radiography, MRI, CT, ultrasound, PET, SPECT machine, and the like. The images from the exam are stored on a PACS (picture archiving and communication server) 1804 for review by a radiologist on a reading workstation (e.g., DICOM workstation 1806). The radiologists' report and related images are saved on a radiology information system (RIS) server 1808. A radiology billing specialist ("coder") 1810 transcribes the radiologist's report into standard codes, e.g., ICD-10 codes. The coded report is also saved in the RIS system 1808. On a periodic or ad hoc basis, a quality analyst 1812 can initiate a process on an RIS server to send exam images and corresponding diagnosis codes to a CAD-and-compare service 1814 for assessment of whether the two agree. The quality analyst or auditor reviews the results on his/her computer. Note that in an alternate embodiment of this diagram, there may be another computer that runs a batch process to gather images and their corresponding diagnoses, send them to the CAD-and-compare service, and aggregate the results.

Figure 19:
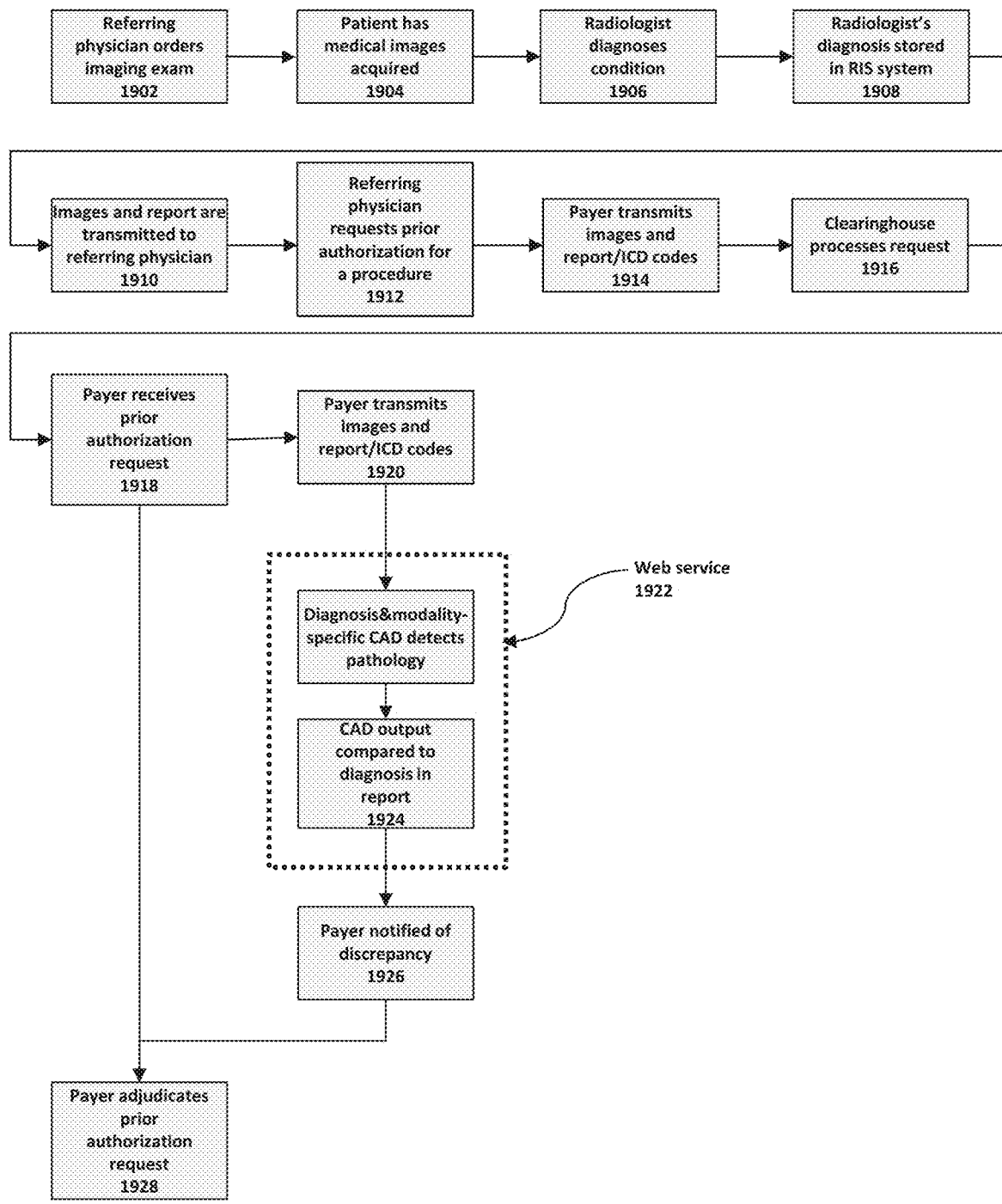
FIG. 19 illustrates an overview of an exemplary workflow that uses a CAD-and-compare service in the process of obtaining prior authorization for a medical procedure that requires medical images to approve.

FIG. 19 illustrates an overview of an exemplary workflow that uses a CAD-and-compare service in the process of obtaining prior authorization for a medical procedure that requires medical images to approve. The process starts with a physician ordering an imaging study for a patient 1902. The patient has the imaging study performed 1904. Next, the radiologist interprets the images 1906 and enters a report into an RIS system 1908. The referring physician receives the radiologist's report via the RIS system 1910, which added the report into the patient's EHR. The referring physician reviews the report (and images, if necessary), determines that a treatment (e.g., surgery) is needed, and has his/her office request prior authorization for the procedure with the patient's insurer 1912. The request often goes from a Payer 1914 through a claims processing clearinghouse 1916 prior to being delivered to the Payer. The Payer receives the prior authorization request 1918 and, as one element of the decision-making process, the claims adjudicator submits the images and diagnosis codes 1920 to a CAD-and-compare service 1922, which returns an assessment 1924 of whether the two agree. The Payer is notified of any discrepancy 1926 and the Payer adjudicates the prior authorization request 1928.

The CAD service for adjudicating medical claims can run different algorithms, each designed to detect a particular pathology on a particular imaging modality. For example, the Payer could send a mammogram and the corresponding radiologist report/codes to the service, and the service would run an X-ray-based breast cancer CAD algorithm. In another example, the Payer could send a chest CT study and corresponding radiologist report/codes to the service, and the serviced would run a CT-based lung nodule CAD algorithm. In this way, new algorithms can be added to the CAD-and-compare service as they are developed.

C. Computing Environment

Figure 20:
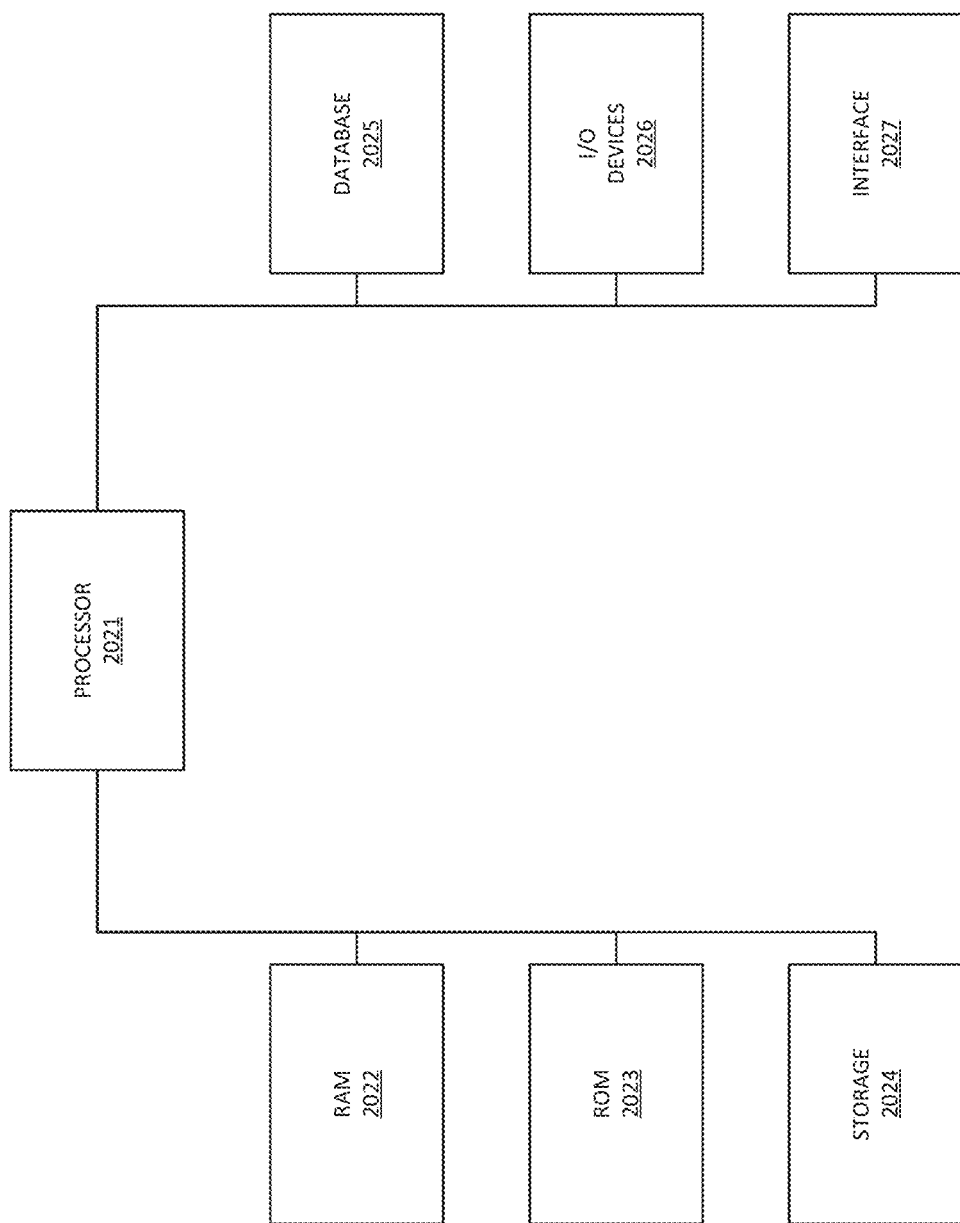
FIG. 20 illustrates an exemplary computer or computing device that can be used for some, a portion of, or all of the set of features and components described herein.

FIG. 20 illustrates an exemplary computer or computing device that can be used for some, a portion of, or all of the features and/or components described herein. All or a portion of the device shown in FIG. 20 may comprise all or any portion of any of the components and devices described herein that may include and/or require a processor or processing capabilities. As used herein, "computer" may include a plurality of computers. The computers may include one or more hardware components such as, for example, a processor 2021, a random access memory (RAM) module 2022, a read-only memory (ROM) module 2023, a storage 2024, a database 2025, one or more input/output (I/O) devices 2026, and an interface 2027. Alternatively and/or additionally, the computer may include one or more software components such as, for example, a computer-readable medium including computer executable instructions for performing a method or methods associated with the exemplary embodiments. It is contemplated that one or more of the hardware components listed above may be implemented using software. For example, storage 2024 may include a software partition associated with one or more other hardware components or more general storage arrangement (e.g., Storage Area Network or "SAN"). It is understood that the components listed above are exemplary only and not intended to be limiting.

Processor 2021 may include one or more processors, each configured to execute instructions and process data to perform one or more functions associated with a computer for asset verification/validation and automated transaction processing. Processor 2021 may be communicatively coupled to RAM 2022, ROM 2023, storage 2024, database 2025, I/O devices 2026, and interface 2027. Processor 2021 may be configured to execute sequences of computer program instructions to perform various processes. The computer program instructions may be loaded into RAM 2022 for execution by processor 2021.

RAM 2022 and ROM 2023 may each include one or more devices for storing information associated with operation of processor 2021. For example, ROM 2023 may include a memory device configured to access and store information associated with the computer, including information for identifying, initializing, and monitoring the operation of one or more components and subsystems. RAM 2022 may include a memory device for storing data associated with one or more operations of processor 2021. For example, ROM 2023 may load instructions into RAM 2022 for execution by processor 2021.

Storage 2024 may include any type of mass storage device configured to store information that processor 2021 may need to perform processes corresponding with the disclosed embodiments. For example, storage 2024 may include one or more magnetic and/or optical disk devices, such as hard drives, CD-ROMs, DVD-ROMs, or any other type of mass media device or system (e.g., SAN).

Database 2025 may include one or more software and/or hardware components that cooperate to store, organize, sort, filter, and/or arrange data used by the computer and/or processor 2021. For example, database 2025 may store information and instructions related to image archives and CAD based on medical images. It is contemplated that database 2025 may store additional and/or different information than that listed above.

I/O devices 2026 may include one or more components configured to communicate information with a user associated with computer. For example, I/O devices may include a console with an integrated keyboard and mouse to allow a user to maintain a database of images, and the like. I/O devices 2026 may also include a display including a graphical user interface (GUI) for outputting information on a monitor. I/O devices 2026 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 2027 may include one or more components configured to transmit and receive data via a communication network, such as the Internet, a local area network, a workstation peer-to-peer network, a direct link network, a wireless network, or any other suitable communication platform. For example, interface 2027 may include one or more modulators, demodulators, multiplexers, demultiplexers, network communication devices, wireless devices, antennas, modems, and any other type of device configured to enable data communication via a communication network.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed:

1. A system for performing computer-aided detection (CAD) using an image of one or more teeth, comprising:
    a computer comprising one or more processors and a memory, wherein the one or more processors of the computer execute computer-executable instructions stored in the memory of the computer causing the computer to:
    receive the image of the one or more teeth;
    segment each of the one or more teeth that comprise the image to determine boundaries between each of the one or more teeth, wherein each tooth of the one or more teeth comprises a separate segmented image;
    number each tooth in the separate segmented images using a tooth-type classifier model, wherein the teeth are numbered according to a standardized numbering system,
    wherein numbering each tooth in the separate segmented images comprises:
        performing a fuzzy-logic process for the numbering each tooth in the separate segmented images comprising:
            identifying a likelihood that each of the separate segmented images contains any of several types of teeth including primary molars, secondary molars, primary canines, secondary canines, secondary premolars, primary incisors, secondary incisors, gaps between teeth, exfoliating teeth, and cropped teeth, wherein the probabilities of tooth types for the teeth are arranged in a tooth probability list of length number of teeth multiplied by a number of tooth types, and wherein the tooth probability list is element-wise multiplied against each row of a matrix to produce a sequence score and tooth numbering is determined by the row with the highest score.

2. The system of claim 1, wherein the standardized numbering system comprises a Universal Numbering System, wherein each tooth is assigned a number from 1-32 (adult teeth) or letter from A-T (deciduous teeth).

3. The system of claim 1, wherein the image comprises an x-ray image of the one or more teeth, an image from a magnetic resonance imaging (MRI) system of the one or more teeth, an image from a computed tomography (CT) system of the one or more teeth, an image from an ultrasound system of the one or more teeth, an image from a positron emission tomography (PET) system of the one or more teeth, or an image from a single-photon emission computed tomography (SPECT) machine of the one or more teeth.

4. The system of claim 1, wherein the one or more processors of the computer execute computer-executable instructions stored in the memory of the computer further causing the computer to:

perform computer-aided detection (CAD) on each of the separate segmented images using a classifier model for restoration detection, wherein the restoration detection identifies teeth with restorations that may produce false negative results from a caries classifier model.

5. The system of claim 4, wherein the classifier model classifies overall image features, said classifier model comprising an image classifier that is trained to identify images that include orthodontia or images that are of poor quality.

6. The system of claim 5, wherein the classifier model comprises a convolutional neural network (CNN).

7. The system of claim 4, wherein the one or more processors of the computer execute computer-executable instructions stored in the memory of the computer further causing the computer to:

exclude separate segmented images with restorations that may produce false negative results from the caries classifier model; and determine whether a tooth in a non-excluded separate segmented image has a caries, or not, using the caries classifier model, wherein the caries classifier is trained to determine whether a tooth has caries.

8. The system of claim 7, wherein the caries classifier model comprises a convolutional neural network (CNN).

9. The system of claim 8, wherein the caries classifier model comprises a region-based convolutional neural network (R-CNN).

10. The system of claim 1, wherein the one or more processors of the computer execute computer-executable instructions stored in the memory of the computer further causing the computer to execute a caries classifier model, said caries classifier model comprising a region-based convolutional neural network (R-CNN), and wherein the one or more processors of the computer execute computer-executable instructions stored in the memory of the computer further cause the computer to perform caries detection of the image by the caries classifier model returning a list or an image of rectangular regions of the image with caries.

11. The system of claim 1, wherein the one or more processors further execute computer-executable instructions to:

segment each of the one or more teeth that comprise the image to separate segmented images by separating upper teeth from lower teeth in the image by identifying an occlusal plane, wherein the occlusal plane is identified by rotating the image several degrees in clockwise and counterclockwise directions, where at each increment a projection of intensity for each image row is summed and the occlusal plane is identified by a valley in the profiles of this projection ("occlusal valley");

examine each column in the rotated image, identify a maximum depth of the occlusal valley in that column, and create an occlusal curve, wherein the occlusal curve is a smoothed curve of the maximum valley depth locations spanned along the rows of the image;

identify boundaries between each tooth or partial tooth that comprises the image, wherein the boundaries are determined independently for an upper and lower set of teeth as determined by the occlusal plane, and wherein the boundaries between each tooth are determined by taking a column-wise projection of intensities between the occlusal curve and an edge of the image, wherein spaces between the teeth are indicated by the valleys in the projections; and use K-means to determine an average position of column numbers in the image that correspond to the interproximal space between teeth.

12. The system of claim 11, wherein the one or more processors further execute computer-executable instructions to:

starting at a row on the occlusal curve that roughly separates a tooth from one next to it, move a rectangular window towards the edge of the image, wherein a tooth segmentation line is chosen to be at a column of this window for which the average intensity in the window is the minimum;

filter out false tooth segmentation curves in the column-wise projections by comparing image intensity along the curve to those of curves translated to the left and right of the segmentation curve, wherein segmentation curves that run through the pulp of a tooth will have more similar intensities to each other, compared to a segmentation curve that runs between the teeth;

determine a distance between intensities, wherein curves for which the intensities are too close to each other are rejected; and output separate segmented images, one for each segmented region.

13. The system of claim 1, wherein the processor further executes computer-executable instructions to place the number assigned to each of the one or more teeth by the tooth-type classifier model in each tooth's separate segmented image.

14. The system of claim 1, wherein the processor further executes computer-executable instructions to place the number assigned to each of the one or more teeth by the tooth-type classifier model in the image of the one or more teeth.

15. A method for performing computer-aided detection (CAD) using an image of one or more teeth, said method comprising:

segmenting and numbering each of the one or more teeth of the image using a computer comprising one or more processors and a memory, wherein the one or more processors of the computer execute computer-executable instructions stored in the memory of the computer causing the computer to:

segment each of the one or more teeth that comprise the image to determine boundaries between each of the one or more teeth, wherein each tooth of the one or more teeth comprises a separate segmented image; and number each tooth in the separate segmented images using a tooth-type classifier model, wherein the teeth are numbered according to a standardized numbering system, wherein numbering each tooth in the separate segmented images comprises:

performing a fuzzy-logic process for the numbering of each tooth in the separate segmented images comprising:

identifying a probability that each of the separate segmented images contains any of a plurality of tooth types including primary molars, secondary molars, primary canines, secondary canines, secondary premolars, primary incisors, secondary incisors, gaps between teeth, exfoliating teeth, and cropped teeth, wherein the probabilities of tooth types for the teeth are arranged in a tooth probability list of length number of teeth multiplied by a number of the tooth types, and wherein the tooth probability list is element-wise multiplied against each row of a matrix to produce a sequence score and tooth numbering is determined by the row with a highest score.

16. The method of claim 15, wherein the standardized numbering system comprises a Universal Numbering System, wherein each tooth is assigned a number from 1-32 (adult teeth) or letter from A-T (deciduous teeth).

17. The method of claim 15, wherein the image comprises an x-ray image of the one or more teeth, an image from a magnetic resonance imaging (MRI) system of the one or more teeth, an image from a computed tomography (CT) system of the one or more teeth, an image from an ultrasound system of the one or more teeth, an image from a positron emission tomography (PET) system of the one or more teeth, or an image from a single-photon emission computed tomography (SPECT) machine of the one or more teeth.

18. The method of claim 15, wherein the one or more processors of the computer execute computer-executable instructions stored in the memory of the computer further causing the computer to:

perform computer-aided detection (CAD) on each of the separate segmented images using a classifier model for restoration detection, wherein the restoration detection identifies teeth with restorations that may produce false negative results from a caries classifier model.

19. The method of claim 18, wherein the classifier model classifies overall image features, said classifier model comprising an image classifier that is trained to identify images that include orthodontia or images that are of poor quality.

20. The method of claim 19, wherein the classifier model comprises a convolutional neural network (CNN).

21. The method of claim 18, wherein the one or more processors of the computer execute computer-executable instructions stored in the memory of the computer further causing the computer to:

exclude separate segmented images with restorations that may produce false negative results from the caries classifier model; and determine whether a tooth in a non-excluded separate segmented image has a caries, or not, using the caries classifier model, wherein the caries classifier is trained to determine whether a tooth has caries.

22. The method of claim 21, wherein the caries classifier model comprises a convolutional neural network (CNN).

23. The method of claim 22, wherein the caries classifier model comprises a region-based convolutional neural network (R-CNN).

24. The method of claim 15, wherein the one or more processors of the computer execute computer-executable instructions stored in the memory of the computer further causing the computer to execute a caries classifier model, said caries classifier model comprising a region-based convolutional neural network (R-CNN), and wherein the one or more processors of the computer execute computer-executable instructions stored in the memory of the computer further causing the computer to perform caries detection of the image by the caries classifier model returning a list or an image of rectangular regions of the image with caries.

25. The method of claim 15, wherein the one or more processors further execute computer-executable instructions to:

segment each of the one or more teeth that comprise the image to separate segmented images by separating upper teeth from lower teeth in the image by identifying an occlusal plane, wherein the occlusal plane is identified by rotating the image several degrees in clockwise and counterclockwise directions, where at each increment a projection of intensity for each image row is summed and the occlusal plane is identified by a valley in the profiles of this projection ("occlusal valley");

examine each column in the rotated image, identify a maximum depth of the occlusal valley in that column, and create an occlusal curve, wherein the occlusal curve is a smoothed curve of the maximum valley depth locations spanned along the rows of the image;

identify boundaries between each tooth or partial tooth that comprises the image, wherein the boundaries are determined independently for an upper and lower set of teeth as determined by the occlusal plane, and wherein the boundaries between each tooth are determined by taking a column-wise projection of intensities between the occlusal curve and an edge of the image, wherein spaces between the teeth are indicated by the valleys in the projections; and use K-means to determine an average position of column numbers in the image that correspond to the interproximal space between teeth.

26. The method of claim 25, wherein the one or more processors further execute computer-executable instructions to:

starting at a row on the occlusal curve that roughly separates a tooth from one next to it, move a rectangular window towards the edge of the image, wherein a tooth segmentation line is chosen to be at a column of this window for which the average intensity in the window is the minimum;

filter out false tooth segmentation curves in the column-wise projections by comparing image intensity along the curve to those of curves translated to the left and right of the segmentation curve, wherein segmentation curves that run through the pulp of a tooth will have more similar intensities to each other, compared to a segmentation curve that runs between the teeth;

determine a distance between intensities, wherein curves for which the intensities are too close to each other are rejected; and output separate segmented images, one for each segmented region.

27. The method of claim 15, wherein the processor further executes computer-executable instructions to place the number assigned to each of the one or more teeth by the tooth-type classifier model in each tooth's separate segmented image.

28. The method of claim 15, wherein the processor further executes computer-executable instructions to place the number assigned to each of the one or more teeth by the tooth-type classifier model in the image of the one or more teeth.

29. A system for performing computer-aided detection (CAD) using an image of one or more teeth, comprising:
- a computer comprising one or more processors and a memory, wherein the one or more processors of the computer execute computer-executable instructions stored in the memory of the computer causing the computer to:
  - segment each of the one or more teeth that comprise the image to form a separate segmented image for each tooth of the one or more teeth that comprise the image; and
  - number each tooth of the separate segmented images using a tooth-type classifier model, wherein the teeth are numbered according to a standardized numbering system,
  - wherein numbering each tooth of the separate segmented images comprises the tooth-type classifier identifying a probability that each of the separate segmented images contains any of a plurality of tooth types, wherein the probabilities of tooth types for the teeth are arranged in a list of length number of teeth multiplied by a number of the plurality of tooth types to form a tooth probability list,
  - and wherein the tooth probability list is element-wise multiplied against each row of a matrix to produce a sequence score and tooth numbering is determined by the row with a highest score.

30. A method for performing computer-aided detection (CAD) using an image of one or more teeth, said method comprising:
- segmenting each of the one or more teeth that comprise the image to form a separate segmented image for each tooth of the one or more teeth that comprise the image; and
- number each tooth in each of the separate segmented images using a tooth-type classifier model, wherein the teeth are numbered according to a standardized numbering system,
- wherein numbering each tooth of the separate segmented images comprises the tooth-type classifier identifying a probability that each of the separate segmented images contains any of a plurality of tooth types, wherein the probabilities of tooth types for the teeth are arranged in a list of length number of teeth multiplied by a number of the plurality of tooth types to form a tooth probability list,
- and wherein the tooth probability list is element-wise multiplied against each row of a matrix to produce a sequence score and tooth numbering is determined by the row with a highest score.

* * * * *